United States Patent [19]

della Valle et al.

[11] Patent Number: 5,202,431

[45] Date of Patent: Apr. 13, 1993

[54] PARTIAL ESTERS OF HYALURONIC ACID

[75] Inventors: Francesco della Valle, Padova; Aurelio Romeo, Rome, both of Italy

[73] Assignee: Fidia, S.p.A., Abano Terme, Italy

[21] Appl. No.: 794,703

[22] Filed: Nov. 20, 1991

Related U.S. Application Data

[60] Continuation of Ser. No. 663,324, Mar. 1, 1991, abandoned, which is a division of Ser. No. 562,267, Aug. 3, 1990, abandoned, which is a division of Ser. No. 339,919, Apr. 19, 1989, Pat. No. 4,965,353, which is a division of Ser. No. 881,454, Jul. 2, 1986, Pat. No. 4,851,521.

[30] Foreign Application Priority Data

Jul. 8, 1985 [IT] Italy ................. 48322 A/85
Jun. 30, 1986 [IT] Italy ................. 48202 A/86

[51] Int. Cl.$^5$ .............. A61K 31/70; C07G 3/00; C07H 1/00
[52] U.S. Cl. .................. 536/55.1; 424/489; 424/423; 514/54; 514/844
[58] Field of Search ............ 536/55.1; 514/54, 844; 264/203, 204; 424/489, 423

[56] References Cited

U.S. PATENT DOCUMENTS

| | | | |
|---|---|---|---|
| 2,515,393 | 7/1950 | Burke | 264/204 |
| 3,402,236 | 9/1968 | Goodwin | 264/203 |
| 3,415,922 | 12/1968 | Carter et al. | 264/203 |
| 3,474,163 | 10/1969 | Jamison | 264/203 |
| 4,141,973 | 2/1979 | Balazs | 514/54 |
| 4,257,999 | 3/1981 | Reinehr et al. | 264/203 |
| 4,328,803 | 5/1982 | Pape | 604/28 |
| 4,344,908 | 8/1982 | Smith et al. | 264/203 |
| 4,352,770 | 10/1982 | Turbak et al. | 264/203 |
| 4,440,711 | 4/1984 | Kwon et al. | 264/203 |
| 4,440,926 | 4/1984 | Mardiguian | 536/21 |
| 4,517,295 | 5/1985 | Bracke et al. | 536/55.1 |
| 4,551,296 | 11/1985 | Kavesh et al. | 264/203 |
| 4,582,865 | 4/1986 | Balazs et al. | 524/29 |
| 4,593,091 | 6/1986 | della Valle et al. | 536/55.1 |
| 4,613,665 | 9/1986 | Larm | 536/55.1 |
| 4,636,524 | 1/1987 | Balazs et al. | 514/781 |
| 4,687,764 | 8/1987 | Kawai et al. | 514/54 |
| 4,695,624 | 9/1987 | Marburg et al. | 536/55.1 |
| 4,696,677 | 9/1987 | Colegrove et al. | 536/55.1 |
| 4,716,224 | 12/1987 | Sakurai et al. | 536/55.1 |
| 4,761,401 | 8/1988 | Couchman et al. | 536/55.1 |
| 4,851,521 | 7/1989 | della Valle et al. | 424/443 |
| 4,882,162 | 11/1989 | Ikada et al. | 424/444 |
| 4,957,744 | 9/1990 | della Valle et al. | 536/55.1 |
| 4,965,353 | 10/1990 | della Valle et al. | 536/55.1 |

FOREIGN PATENT DOCUMENTS 0103026 7/1980 European Pat. Off. .

(List continued on next page.)

OTHER PUBLICATIONS

Lanette Sx British Pharmacopoeia 1980, vol. 1, pp. 172-173.

(List continued on next page.)

Primary Examiner—Ronald W. Griffin
Attorney, Agent, or Firm—Birch, Stewart, Kolasch & Birch

[57] ABSTRACT

The invention concerns the esters of hyaluronic acid in which all or only a portion of the carboxylic groups of the acid are esterified, and the salts of the partial esters with metals or with pharmacologically acceptable organic bases.

The compounds possess interesting and precious bioplastic and pharmaceutical properties and may be used in innumerable fields, including cosmetics, surgery and medicine. The invention also includes pharmaceutical preparations containing, as an active ingredient, one or more hyaluronic acid esters, or a salt thereof as described above, as well as medicaments containing:

1) a pharmacologically active substance or an association of pharmacologically active substances and
2) a carrying vehicle containing a total or partial ester of hyaluronic acid. The invention includes also various uses of the hyaluronic esters or of the above mentioned medicaments, such as in medicine, surgery or cosmetics.

The invention also relates to a new procedure for the preparation of polysaccharide esters containing carboxylic groups, such as in particular the above mentioned hyaluronic acid esters.

5 Claims, No Drawings

FOREIGN PATENT DOCUMENTS

| | | |
|---|---|---|
| 0044228 | 1/1982 | European Pat. Off. . |
| 0138572 | 4/1985 | European Pat. Off. . |
| 0224987 | 6/1987 | European Pat. Off. . |
| 3434082 | 7/1985 | Fed. Rep. of Germany . |
| 56-29597 | 3/1981 | Japan . |
| 58-37001 | 3/1983 | Japan . |
| WO866728 | 11/1986 | PCT Int'l Appl. . |
| 2151244A | 7/1985 | United Kingdom . |

OTHER PUBLICATIONS

P. R. Watson et al., Carbohydrate Research, vol. 46, (1976) pp. 259–265.

L. Kenne et al., Carbohydrate Research, vol. 84, (1980) pp. 184–186.

R. H. Cundiff et al., analytical Chemistry, vol. 33 (1961) pp. 1028–1030.

Farmacopea Ufficiale Della Rupubblica Italiana F.U. IX, pp. 844–847.

E. A. Balazs, Healon, A Guide to its use in Ophtalmic Surgery ed. D. Miller & R. Stegman, Chapt. 1, pp. 5–28.

A. Steiner et al., Industrial and Engineering Chemistry, vol. 43 (1961) p. 2073.

Chemical Abstract, vol. 80. No. 17, Apr. 29, 1974, p. 146, No. 92658y Vikha et al.

Journal of Bacteriology, vol. 139, No. 3, Sep. 1979, pp. 1065–67, Jager et al.

Chemical Abstract, vol. 68, No. 7, Feb. 12, 1968, p. 2627, No. 27273g.

Patent Abstracts of Japan, No. 88, vol. 9, JP-A-59 219 209.

Jeanloz et al., J. Biol. Chem., vol. 186 (1950).

Jeanloz et al., J. Biol. Chem. vol. 194, pp. 141–150 (1952).

Jeanloz et al., Helvetical Chimica Acta, vol. 35, pp. 262–271 (1952).

PARTIAL ESTERS OF HYALURONIC ACID

This application is a continuation of application Ser. No. 07/663,324 filed on Mar. 1, 1991, now abandoned, which is a divisional of copending application Ser. No. 07/562,267 filed Aug. 3, 1990, now abandoned, which is a divisional of application Ser. No. 07/339,919 filed Apr. 19, 1989, now U.S. Pat. No. 4,965,353, which is a divisional of application Ser. No. 06/881,454 filed Jul. 2, 1986, now U.S. Pat. No. 4,851,521. The entire contents of which are hereby incorporated by reference.

BACKGROUND AND FIELD OF THE INVENTION

The present invention relates to new polysaccharide esters and more precisely esters of hyaluronic acid and their use in the pharmaceutical and cosmetic fields, and in the field of biodegradable plastic materials. The invention therefore includes new medicaments, cosmetic, medical and surgical articles.

The term "hyaluronic acid" (also referred to as "HY" hereinafter) is used in literature to designate an acidic polysaccharide with various molecular weights constituted by residues of D-glucuronic acid and N-acetyl-D-glucosamine, which naturally occur in cellular surfaces, in the basic extracellular substances of the connective tissues of vertebrates, in the synovial fluid of joints, in the vitreous humor of the eye, in the tissue of the human umbilical cord and in cocks' combs.

Hyaluronic acid plays an important role in the biological organism, firstly as a mechanical support of the cells of many tissues, such as the skin, the tendons, the muscles and cartilage and it is therefore the main component of the intracellular matrix. But hyaluronic acid also performs other functions in the biological processes, such as the hydration of tissues, lubrication, cellular migration, cell function and differentiation. (See for example A. Balazs et al., Cosmetics & Toiletries, No. 5/84, pages 8-17). Hyaluronic acid may be extracted from the above mentioned natural tissues, such as. cocks' combs, or also from certain bacteria. Today, hyaluronic acid may also be prepared by microbiological methods. The molecular weight of whole hyaluronic acid obtained by extraction is in the region of 8-13 million. However, the molecular chain of the polysaccharide can be degraded quite easily under the influence of various physical and chemical factors, such as mechanical influences or under the influence of radiation, hydrolyzing, oxydizing or enzymatic agents. For this reason often in the ordinary purification procedures of original extracts, degraded fractions with a lower molecular weight are obtained (See Balazs et al. cited above). Hyaluronic acid, its molecular fractions and the respective salts have been used as medicaments and their use is also proposed in cosmetics (see for example the above mentioned article by Balazs et al. and the French Patent No. 2478468).

As a therapeutic agent, hyaluronic acid and its salts have been used especially in therapy for arthropathies, such as in veterinary medicine for the cure of arthritis in horses [Acta Vet. Scand. 167, 379 (1976)]. As an auxilary and substitutional therapeutic agent for natural tissues and organs, hyaluronic acid and its molecular fractions and their salts have been used in ophthalmic surgery (see for example Balazs et al., Modern Problems in Ophthalmology, Vol. 10, 1970, p. 3—E. B. Strieff, S. Karger eds., Basel; Viscosurgery and the Use of Sodium Hyaluronate During Intraocular Lens Implantation, Paper presented at the International Congress and First Film Festival on Intraocular Implantation, Cannes, 1979; U.S. Pat. No. 4,328,803 with a summary of the literature on the uses of HY in ophthalmology; and U.S. Pat. No. 4,141,973.

In the application for Italian Patent No. 49 143A83 of Oct. 11, 1983, a molecular fraction of hyaluronic acid is described which can be used, for example as sodium salt, for intraocular and intraarticular injections suitable for the substitution of internal fluids of the eye and in arthropathy therapies, respectively. See also co-pending U.S. application Ser. No. 06/756,824 filed on Jul 19, 1985, now abandoned, which is hereby incorporated by reference.

Hyaluronic acid may also be used as an additive for a wide variety of polymeric materials used for medical and surgical articles, such as polyurethanes, polyesters, polyolefins, polyamides, polysiloxanes, vinylic and acrylic polymers and carbon fibers with the effect of rendering these materials biocompatible. In this case the addition of HY or one of its salts is effected for example by covering the surface of such materials, by dispersion in the same or by both of these procedures. Such materials may be used for the manufacture of various sanitary and medical articles, such as cardiac valves, intraocular lenses, vascular clips, pacemakers and such (see U.S. Pat. No. 4,500,676).

Although the term "hyaluronic acid" is commonly used in an improper sense, meaning, as can be seen from above, a whole series of polysaccharies with alternations of residues of D-glucuronic acid and N-acetyl-D-glucosamine with varying molecular weights or even degraded fractions of the same, and although the plural form "hyaluronic acids" may seem more appropriate, the discussion herein shall continue to use the singular form to refer to hyaluronic acid in its various forms including its molecular fractions, and the abbreviation "HY" will also often be used to describe this collective term.

Relative to the esters of hyaluronic acid, there is a description in the literature of the methyl ester of a hyaluronic acid with a high molecular weight obtained by extraction from human umbilical cords [Jeanloz et al., J. Biol. Chem. 186 (1950), 495-511, and Jager et al., J. Bacteriology 1065-1067 (1979)]. This ester was obtained by treatment of free hyaluronic acid with diazomethane in ether solution and in it substantially all the carboxylic groups proved to be esterified. Furthermore, methyl esters of oligomers of HY with about between 5 and 15 disaccharide units have also been described [see Biochem. J. (1977) 167, 711-716]. Also described is a methyl ester of hyaluronic acid etherified with methyl alcohol in a part of the hydroxyl alcohol groups [Jeanloz et al., J. Biol. Chem. 194 (1952), 141-150; and Jeanloz et al , Helvetica Chimica Acta 35 (1952), 262-271]. No biological activity and therefore no pharmaceutical use has been reported for these esters.

DETAILED DESCRIPTION OF THE INVENTION

According to an object of the present invention the esters of hyaluronic acid with aliphatic, araliphatic, cycloaliphatic or etherocyclic alcohols, in which are esterified all or only a part of the carboxylic groups of the acid, and the salts of the partial esters with metals or with organic bases, biocompatible or acceptable from a pharmacological point of view, possess interesting and precious bio-plastic and pharmaceutical properties and may be used in innumerable fields, including cosmetics, surgery and medicine. In the case of hyaluronic acid, in which the new products qualitatively possess the same or similar physical-chemical, pharmacological and therapeutic properties, they are considerably more stable, especially regarding the action of the natural enzymes responsible for the degradation of the polysaccharide molecule in the organism, such as especially hyaluronidase, and they, therefore, conserve the above mentioned properties for very long periods.

A first group of esters according to the present invention, useful in therapy as well as in the other above mentioned fields, is therefore represented by those in which the qualities of hyaluronic acid itself dominate and may be exploited. Such esters derive from alcohols of the above mentioned series which do not themselves possess a notable pharmacological action, such as for example the saturated alcohols of the aliphatic series or simple alcohols of the cycloaliphatic series.

A second group of esters useful in therapy is represented, on the other hand, by the esters in which the pharmacological qualities of the alcohol component dominate. That is, esters of HY with pharmacologically active alcohols, such as steroid alcohols, such as those of the cortisone type with an antiinflammatory action. These compounds possess properties qualitatively similar to those of the alcohol, but with a more differentiated range of action, compared also to already known esters, ensuring a better balanced, constant and regular pharmacological action, and usually obtaining a marked retard effect.

A third group of esters of HY according to the present invention, and which represent a particularly original and useful aspect, regards the esters with a more mixed character compared to the two previous groups; That is, esters in which a part of the carboxylic groups of HY are esterified with a pharmacologically active alcohol and another part with a pharmacologically indifferent alcohol, or one whose activity is negligible. By suitably dosing percentages of the two types of alcohols as an esterifying component, it is possible to obtain esters with the same pharmacological activity as the pharmacologically active alcohol, without the specific activity of hyaluronic acid, but having those above mentioned qualities of better stability and bioavailability, with respect to the activity desired and characteristic of the pharmacologically active alcohol and due to the ester groups of the pharmacologically inert alcohol.

A fourth group of esters is represented by those of a mixed character in which the ester groups derive from two different therapeutically active substances. In this case also the esters may be partial or total, that is, only some carboxylic groups are esterified by two different therapeutically active alcohols, for example by one cortisone steroid and by an antibiotic or by a phenothiazine, while the carboxylic groups may be free or salified, for example with alkaline metals, particularly with sodium, or all the carboxylic groups are esterified with the above mentioned alcohols. It is, however, also possible to prepare esters with three or more alcohol components, such as esters in which a part of the carboxylic groups are esterified with a therapeutically active alcohol, another part with another therapeutically active alcohol, a third part with a therapeutically inactive alcohol and a fourth part is possibly salified with a metal and with a therapeutically active or inactive base or comprises carboxylic groups in a free form.

In the above mentioned esters in which some of the carboxylic acid groups remain free, these may be salified with metals or organic bases, such as with alkaline or alkaline earth metals or with ammonia or nitrogenous organic bases.

Most of the esters of HY, unlike HY itself, present a certain degree of solubility in organic solvents. This solubility depends on the percentage of esterified carboxylic groups and on the type of alkyl group linked with the carboxyl. Therefore an HY compound with all its carboxylic groups esterified presents, at room temperature, good solubility for example in dimethylsulfoxide (the benzyl ester of HY dissolves in DMSO in a measure of 200 mg/ml). Most of the total esters of HY present also, unlike HY and especially its salts, poor solubility in water.

The previously mentioned solubility characteristics, together with particular and notable viscoelastic properties, allow the use of HY esters to obtain sanitary and medical preparations which are insoluble in saline and which have the particular, desired form. These materials are obtained by preparing a solution of an HY ester in an organic solvent, forming the very viscose solution into the form of the desired article, and extracting the organic solvent with another solvent which mixes with the first, but in which the HY ester is insoluble.

The esters of hyaluronic acid according to the present invention are all new, except for the aforementioned methyl ester of hyaluronic acid extracted from human umbilical cords and the methyl esters of the above mentioned oligomers of HY. Also new, therefore, are partial esters of hyaluronic acid with methyl alcohol and their salts with metal or organic bases. The biological and pharmacological activities of the above mentioned methyl esters described in literature, were unknown, as were their excellent bioplastic qualities and high stabilty. Also unknown, therefore, was the use of such esters for the preparation of medicaments, cosmetics, sanitary and surgical articles and other new products discussed above which are a part of the present invention. In particular therefore, the pharmaceutical preparations containing the already known methyl esters of HY are also new.

Finally, the present invention also includes the use of the above mentioned new products and of the above mentioned known methyl ester, as vehicles for active pharmaceutical substances, and medicaments including the above mentioned esterified derivatives of hyaluronic acid and one or more of such active substances. In such medicaments the hyaluronic ester or one of its salts is preferably derived from pharmacologically inactive alcohols, but may also represent an ester derived from a pharmacologically active alcohol and have itself a pharmacological activity. The vehicling action of the component represented by the hyaluronic ester or one of its salts is to be observed in a more satisfactory assimilation of the active substance in conditions which are particularly compatible with the biological environment of the organ to be treated. This is especially the case in the field of ophthalmology. Of these medicaments containing a hyaluronic ester as vehicle, those for topical use are particularly important. The main object of the present invention is, therefore, represented by the total or partial esters of hyaluronic acid with alcohols of the aliphatic, araliphatic, cycloaliphatic or heterocyclic series and by the salts of such partial esters with inorganic or organic bases, with the exception of the methyl ester of hyaluronic acid in which substantially all the carboxylic groups are esterified.

A second object of the present invention is represented by the pharmaceutical preparations containing as their active ingredient one or more esters of hyaluronic acid or one of their salts as described above, including the total methyl ester of hyaluronic acid, and the use of such esters for therapeutic uses.

A third object of the present invention is represented by medicaments including:

1) a pharmacologically active substance or an association of pharmacologically active substances and 2) a carrying vehicle made up of a total or partial ester of hyaluronic acid with alcohols of the aliphatic, araliphatic, cycloaliphatic or heterocyclic series or of the salt of such partial esters with inorganic or organic bases, with the addition, if desired, of hyaluronic acid or one of its salts with inorganic or organic bases, and by the use of such medicaments for therapeutic uses.

A fourth object of the present invention is represented by the use of the esters and their salts as described above in cosmetics, and by cosmetic articles containing such esters.

A fifth object of the present invention is represented by the use of the esters and their salts as described above for the manufacture of sanitary and surgical plastic articles and by these articles themselves.

Another use of the new and the known esters according to the invention refers to the manufacture of sanitary, cosmetic and surgical articles in which the hyaluronic esters act as vehicles for the basic substances which serve this purpose, such as the various polymers mentioned above.

Another object of the invention is finally represented by the procedures for the preparation of the esters of hyaluronic acid and of the salts of the partial esters.

Alcohols of the aliphatic series to be used as esterifying components of the carboxylic groups of hyaluronic acid according to the present invention are for example those with a maximum of 34 carbon atoms, which may be saturated or unsaturated and which may possibly also be substituted by other free functional or functionally modified groups, such as amine, hydroxyl, aldehyde, ketone, mercaptan, or carboxyl groups or by groups derived from these, such as hydrocarbyl or di-hydrocarbylamine groups (from now on the term "hydrocarbyl" will be used to refer not only to monovalent radicals of hydrocarbons such as the $C_nH_{2n+1}$ type, but also bivalent or trivalent radicals, such as "alkylenes" $C_nH_{2n}$ or "alkylidenes" $C_nH_{2n}$), ether or ester groups, acetal or ketal groups, thioether or thioester groups, and esterified carboxyl or carbamide groups and carbamide substituted by one or more hydrocarbyl groups, by nitrile groups or by halogens.

Of the above mentioned groups containing hydrocarbyl radicals, these are preferably lower aliphatic radicals, such as alkyls, with a maximum of 6 carbon atoms. Such alcohols may also be interrupted in the carbon atom chain by heteroatoms, such as oxygen, nitrogen and sulfur atoms. Preferred are alcohols substituted with one or two of the said functional groups.

Alcohols of the above mentioned group which are preferably to be used within the bounds of the present invention are those with a maximum of 12, and especially 6 carbon atoms, and in which the hydrocarbyl atoms in the above mentioned amine, ether, ester, thioether, thioester, acetal, ketal groups represent alkyl groups with a maximum of 4 carbon atoms, and also in the esterified carboxyl or substituted carbamide groups the hydrocarbyl groups are alkyls with the same number of carbon atoms, and in which in the amine or carbamide groups may be alkylenamine or alkylencarbamide groups with a maximum of 8 carbon atoms. Of these alcohols special mention should be given to those which are saturated and not substituted such as the methyl, ethyl, propyl, and isopropyl alcohols, normal butyl alcohol, isobutyl alcohol, tertiary butyl alcohol, the amyl, pentyl, hexyl, octyl, nonyl and dodecyl alcohols and, above all, those with a linear chain, such as normal octyl and dodecyl alcohols. Of the substituted alcohols of this group, the bivalent alcohols should be listed, such as ethyleneglycol, propyleneglycol and butyleneglycol, the trivalent alcohols such as glycerine, the aldehyde alcohols such as tartronic alcohol, the carboxylic alcohols such as lactic acids, for example glycolic acid, malic acid, the tartaric acids, citric acid, the aminoalcohols, such as normal aminoethanol, aminopropanol, normal aminobutanol and their dimethylated and diethylated derivatives in the amine function, choline, pyrrolidinylethanol, piperidinylethanol, piperazineylethanol and the corresponding derivatives of normal propyl or normal butyl alcohol, monothioethyleneglycol or its alkyl derivatives, such as the ethyl derivative in the mercaptan function.

Of the higher saturated aliphatic alcohols the following should be mentioned: cetyl alcohol and myricyl alcohol, but for the aim of the present invention the higher unsaturated alcohols with one or two double bonds, are especially important, such as especially those contained in many essential oils and with affinity to terpene, such as citronellol, geraniol, nerol, nerolidol, linalool, farnesol, phytol. Of the unsaturated lower alcohols it is necessary to consider allyl alcohol and propargyl alcohol. Of the araliphatic alcohols special attention should be given to those with only one benzene residue and in which the aliphatic chain has a maximum of 4 carbon atoms, which the benzene residue can be substituted by between 1 and 3 methyl or hydroxyl groups or by halogen atoms, especially by chlorine, bromine and iodine, and in which the aliphatic chain may be substituted by one or more functions chosen from the group containing fee amine groups or mono- or dimethylated or by pyrrolidine or piperidine groups. Of these alcohols special attention should be given to benzyl alcohol and phenetyl alcohol.

The alcohols of the cycloaliphatic or aliphatic-cycloaliphatic series may derive from mono- or polycyclic hydrocarbons, may preferably have a maximum of 34 carbon atoms, may be unsubstituted and may contain one or more substituents, such as those mentioned above for the aliphatic alcohols. Of the alcohols derived from cyclic monoannular hydrocarbons, special mention should be given to those with a maximum of 12 carbon atoms, the rings with preferably between 5 and 7 carbon atoms, which may be substituted for example by between one and three lower alkyl groups, such as methyl, ethyl, propyl or isopropyl groups. As specific alcohols of this group the following can be mentioned: cyclohexanol, cyclohexanediol, 1,2,3 cyclohexanetroil and 1,3,5 cyclohexanetriol (phloroglucitol), inositol, and the alcohols which derive from p-methane such as carvomenthol, menthol, and α- γ terpineol, 1-terpineol, 4-terpineol and piperitol, or the mixture of these alcohols known as "terpineol", 1,4- and 1,8 terpin. Of the alcohols which derive from hydrocarbons with condensed rings, such as those of the thujane, pinane or comphane, the following can be mentioned: thujanol, sabinol, pinol hydrate, D and L-borneol and D and L-isoborneol.

Aliphatic-cycloaliphatic polycyclic alcohols to be used for the esters of the present invention are sterols, cholic acids and steroids, such as sexual hormones and their synthetic analogues, especially corticosteroids and their derivatives. It is therefore possible to use: cholesterol, dihydrocholesterol, epidihydrocholesterol, coprostanol, epicoprostanol, sitosterol, stigmasterol, ergosterol, cholic acid, deoxycholic acid, lithocholic acid, estriol, estradiol, equilenin, equilin and their alkylate derivatives, as well as their ethynyl or propynyl derivatives in position 17, such as 17 α-ethynlestradiol or 7 α-methyl-17 α-ethynyl-estradiol, pregnenolone, pregnanediol, testosterone and its derivatives, such as 17 α-methyltestosterone, 1,2-dehydrotestosterone and 17 α-methyl-1,2-dehydrotesterone, the alkynylate derivatives in position 17 of testosterone and 1,2-dehydrotestosterone, such as 17 α-ethynyltestosterone, 17 α-propynyltestosterone, norgestrel, hydroxyprogesterone, corticosterone, deoxycorticosterone, 19-nortestosterone, 19-nor-17 α-methyltestosterone and 19-nor-17 α-ethynyltestosterone, antihormones such as cyproterone, cortisone, hydrocortisone, prednisone, prednisolone, fluorocortisone, dexamethasone, betamethansone, paramethasone, flumethasone, fluocinolone, fluprednylidene, clobetasol, beclomethasone, aldosterone, deoxycorticosterone, alfaxolone, alfadolone, bolasterone. As esterifying components for the esters of the present invention the following are useful: genins (aglycons) of the cardioactive glucosides, such as digitoxigenin, gitoxigenin, digoxigenin, strophanthidin, tigogenin and saponins.

Other alcohols to be used according to the invention are the vitamin ones, such as axerophthol, vitamins $D_2$ and $D_3$, aneurine, lactoflavine, ascorbic acid, riboflavine, thiamine, pantothenic acid.

Of the heterocyclic acids the following can be considered as derivatives of the above mentioned cycloaliphatic or aliphatic-cycloaliphatic alcohols if their linear or cyclic chains are interrupted by one or more, for example by between one and three heteroatoms, for instance chosen from the group formed by —O—, —S—, —N, —NH— and in these there may be one or more unsaturated bonds, for example double bonds, in particular between one and three, thus including also heterocyclic compounds with aromatic structures. For example the following should be mentioned: furfuryl alcohol, alkaloids and derivatives such as atropine, scopolamine, cinchonine, la cinchonidine, quinine, morphine, codeine, nalorphine, N-butylscopolammonium bromide, ajmaline; phenylethylamines such as ephedrine, isoproterenol, epinephrine; phenothiazine drugs such as perphenazine, pipothiazine, carphenazine, homofenazine, acetophenazine, fluophenazine, N-hydroxyethylpromethazine chloride; thioxanthene drugs such as flupenthixol and clopenthixol; anticonvulsants such as meprophendiol; antipsychotics such as opipramol; antiemetics such as oxypendyl; analgesics such as carbetidine and phenoperidine and methadol; hypnotics such as etodroxizine; anorexics such as benzidrol and diphemethoxidine; minor tranquilizers such as hydroxyzine; muscle relaxants such as cinnamedrine, diphylline, mephenesin, methocarbamol, chlorphenesin, 2,2-diethyl-1,3-propanediol, guaifenesin, hydrocilamide; coronary vasodilators such as dipyridamole and oxyfedrine; adrenergic blockers such as propanolol, timolol, pindolol, bupranolol, atenolol, metoprolol, practolol; antineoplastics such as 6-azauridine, cytarabine, floxuridine; antibiotics such as chloramphenicol, thiamphenicol, erythromycin, oleandomycin, lincomycin; antivirals such as idoxuridine; peripheral vasodilators such as isonicotinyl alcohol; carbonic anhydrase inhibitors such as sulocarbilate; antiasthmatic and antiinflammatories such as tiaramide; sulfamidics such as 2-p-sulfanilonoethanol.

As discussed above, in some cases hyaluronic acid esters may be of interest where the ester groups derive from two or more therapeutically active hydroxylic substances, and naturally all possible variants may be obtained. Especially interesting are the substances in which two types of different ester groups deriving from drugs of a hydroxylic character are present and in which the remaining carboxyl groups are free, salified with metals or with one or various bases listed later, possibly also bases being themselves therapeutically active, for example with the same or similar activity as that of the esterifying component. In particular, it is possible to have hyaluronic esters deriving on the one hand from an antiinflammatory steroid, such as one of those mentioned previously, and on the other hand from a vitamin, from an alkaloid or from an antibiotic, such as one of those listed.

The degree of esterification of hyaluronic acid with the above mentioned alcohols depends firstly on the special properties to be obtained in the various fields of application, for example a greater or lesser lipophilia or hydrophilia with respect to certain tissues such as the skin.

Normally, a high degree of esterification up to total esterification of hyaluronic acid increases its lipophilic character and therefore lessens its solubility in water. For a therapeutic use of the new esters of this invention, for example, it is especially important to regulate the degree of esterification in order to ensure, despite a good and increased level of lipophilia compared to hyaluronic acid or its sodium salt, sufficient hydrosolublity, for example, a solubility of 10 mg/ml. Naturally it is necessary to bear in mind the influence of the molecular size of the same esterifying component, which usually influences hydrosolubility in an inversely proportional manner. As has already been said, the esterification of the carboxylic groups of hyaluronic acid may play various roles, which may be useful in different fields, for example in medicine using the esters as therapeutic agents or in surgery using them as plastic articles. For use in therapy, it has already been said that it is possible to consider the esterification of an alcohol which is itself therapeutically active, such as an antiinflammatory cortisteroid, with hyaluronic acid as a means to improve its therapeutic efficacy.

Regarding similar therapeutically active alcohols, hyaluronic acid acts therefore as a particularly efficient vehicle which is perfectly compatible with the biological environment. In the above list of alcohols to be used for esterification according to the present invention, there appear several of these pharmacologically active alcohols and therefore the possible applications of the corresponding esters are apparent as the indications are the same as those for the free alcohols. Again, as has already been said, in partial esters with therapeutically active alcohols it is possible to esterify part or all of the remaining carboxylic groups of the hyaluronic component with pharmacologically inert alcohol, such as the saturated lower aliphatic alcohols, such as ethyl or isopropyl alcohol.

A particularly interesting aspect of the present invention is the possibility of preparing more stable drugs than those available at present. It is possible therefore on the one hand to prepare esters of hyaluronic acid with therapeutically inactive alcohols for use in typical indications of hyaluronic acid itself, such as for intra-articular injections, where the ester acts as a lubricant. Due to the improved stability of the esters relative to hyaluronidase as compared to the free acid, it is possible to obtain quite a considerable prolonged action. On the other hand, it is possible to obtain drugs with a "retard" actions for the above-mentioned esters of HY with therapeutically active alcohols, possibly also salified with therapeutically active bases. The liberation of the active alcohols due to esterase and that of the salified groups due to the hydrolitic action is very slow.

For cosmetic use it is preferable to use total or partial esters of hyaluronic acid with pharmacologically inert alcohols, such as saturated or unsaturated aliphatic alcohols, for example non-substituted alcohols of this type with a straight or ramified chain, for example with between 1 and 8 carbon atoms, such as those specifically mentioned previously. Particularly interesting are those unsaturated alcohols, such as with one or more double bonds, such as vinyl or allyl alcohols and their condensed derivatives, such as especially polyvinyl alcohols or polyvalent alcohols, such as glycerine. In this case also it is possible to use, according to the intended purpose, mixed esters.

Also useful are cycloaliphatic alcohols, such as derivatives of cyclopentane or cyclohexane and their derivatives substituted by lower alkyl groups, such as alkyls with between 1 and 4 carbon atoms, especially by methyl groups. Of particular interest are also esters with cycloaliphatic and aliphatic alcohols—cycloaliphatics derived from terpene, such as those mentioned above and from therapeutically active alcohols, and which may also be used in cosmetics.

The alcohols to be used preferably to make articles for sanitary and surgical use are essentially the same as those listed above for cosmetic use. In the partial esters according to the invention the percentage of esterified groups may vary greatly in relation to the use for which the product is intended, and that is above all with regard to the use in the various fields of application mentioned above.

Of particular interest however are those partial esters in which at least 5% and at most 90% of all the carboxylic groups of HY are esterified, and especially those with an esterified percentage of between 50 and 80%.

The ratio between the number of different types of ester groups may obviously also vary in the mixed partial esters. For example in the case of two types of such groups, the ratio varies preferably between 0:1:1 and 1:01, and the same is true of total esters. For the esters intended for therapeutic use the ratio varies preferably between 0.5:1 and 1:0.5. Such ratios are preferably also valid for total esters and, in the partial esters, they are to be taken preferably with reference to the percentages mentioned above regarding the inclusive number of esterified groups.

In the partial esters of the invention the non-esterified carboxylic groups may be kept free or may be salified. For the formation of such salts the bases are chosen according to the criterion of these for which the product is intended. It is possible to form inorganic salts deriving from alkaline metals, such as potassium and especially sodium and ammonium, or deriving from alkaline earth metals, such as calcium, or magnesium or aluminum salts.

Particularly interesting are the salts with organic bases, especially nitrogenized bases and therefore aliphatic, arylaliphatic, cycloaliphatic or heterocyclic amines.

These ammonic salts may derive from therapeutically acceptable but inactive amines or from amines with therapeutic action. Of the former the aliphatic amines above all should be considered, such as mono- di- and tri-alkylamines with alkyl groups having a maximum of 18 carbon atoms or arylalkylamines with the same number of carbon atoms in the aliphatic part and where aryl means a benzene group possibly substituted by 1 and 3 methyl groups or halogen atoms or hydroxyl groups. The biologically inactive bases for the formation of salts may also be cyclic such as monocyclic alkylenamines with cycles of between 4 and 6 carbon atoms, possibly interrupted in the cycle by heteroatoms chosen from the group formed by nitrogen, oxygen and sulfur, such as piperidine or morpholine, and may be substituted for example by aminic or hydroxylic functions, such as aminoethanol, ethylendiamine, ephedrine or choline.

It is also possible to form the quarternary ammonium salts of the partial esters, for example the salts of tetraalkylammonium with the above mentioned number of carbon atoms and preferably salts of such a type in which the fourth alkyl group has between 1 and 4 carbon atoms, for example a methyl group.

Among the biologically active amines whose therapeutic actions may be put to use, are included all the nitrogenized and basic drugs such as those included in the following groups: alkaloids, peptides, phenothiazines, benzodiazepines, thioxanthenes, hormones, vitamins, anticonvulsants, antipsychotics, antiemetics, anesthetics, hypnotics, anorexics, transquilizers, muscle relaxants, coronary vaso dilators, antineoplastics, antibiotics, antibacterials, antivirals, antimalarials, carbonic anhydrase inhibitors, non-steroid antiinflammatory agents, vasoconstrictors, cholinergic agonists, cholinergic antagonists, adrenergic agonists, adrenergic antagonists, narcotic antagonists.

All those drugs with basic nitrogenized groups listed in the invention and regarding the use of the esters may be quoted as examples.

According to a particular aspect of the present invention the new hyaluronic esters and their salts may be used as an excellent vehicle for therapeutically active substances. To this end it is possible to use the total esters or the partial esters of the salified partial esters in the remaining carboxylic groups, for example with one of the above mentioned substances therapeutically acceptable but not biologically active, above all with alkaline metals, for example sodium. These are the above mentioned medicaments made by association containing two components:

Component (1)—a pharmacologically active substance or an association of two or more active substances; and Component (2)—a carrying vehicle comprising a partial or total ester of hyaluronic acid with an alcohol, or the salts of such partial esters with an organic or inorganic base, optionally with the addition of hyaluronic acid or a salt thereof with an inorganic or organic base.

The hyaluronic esters to be used in these medicaments are above all those in which the esterifying alcohol is not itself pharmacologically active, for example a simple aliphatic alcohol, as described above. Medicaments of this type in which the ester also is pharmacologically active, for example a simple aliphatic alcohol, as described above. Medicaments of this type in which the ester also is pharmacologically active are not excluded from this aspect of the invention, as for example in the case of one of the esters described above deriving from alcohols with pharmacological action.

In the same way, the invention also includes medicaments of this type in which the esters of Component (2) are salified also with therapeutically active bases. These bases may be the same pharmacologically active substances vehicled in the hyaluronic ester, and the mixture in this case, as described below, therefore contains salts of a partial ester of hyaluronic acid with therapeutically active bases, possibly in the presence of an excess of active base component (1). The case may on the other hand present itself where the vehicled substance is not of a basic nature, and free carboxylic groups in the hyaluronic ester are still salified with therapeutically active bases.

The use of hyaluronic esters as a vehicle allows therefore the preparation of the new medicaments described above, including 1) a pharmacologically active substance or an association of two or more of such substances and 2) a hyaluronic ester as described above or one of its salts, and such medicaments are a further object of the invention. In such medicaments, if partial esters of HY are used, the possible salification of the remaining carboxylic groups is carried out preferably with therapeutically neutral inorganic or organic bases, especially with alkaline metals such as sodium or ammonium. Should the active substance component (1) or a corresponding association of substances have basic groups, such as for example antibiotics containing amine groups, and if partial esters of hyaluronic acid should be used with remaining free carboxylic groups, the corresponding salts are formed between the carboxylic groups and these basic substances. The new medicaments therefore include in particular partial esters of hyaluronic acid partially and totally salified with pharmacologically active substances and of a basic character. As described above, particularly important are the associated medicaments of the type described here, in which Component (1) is a pharmacologically active substance for topical use.

The use of hyaluronic esters as a vehicle for drugs to be applied topically is particularly useful in ophthalmology where a particular compatibility is to be observed for the new products with the corneal epithelium, and therefore excellent tolerability, without any sensitization effects. Furthermore, when the medicaments are administered in the form of concentrated solutions with elastic-viscose characteristics or in solid form, it is possible to achieve homogenous and stable films which are perfectly transparent and adhesive on the corneal epithelium, guaranteeing prolonged bioavailability of the drug and therefore representing excellent preparations with a retard effect.

Such ophthalmic medicaments are particularly valuable in the veterinary field, considering for example that at present there are no veterinary specialities for oculistic use containing chemotherapeutic agents. Indeed, preparations intended for human use are usually used, and these do not always guarantee a specific range of action or they do not make allowances for the particular conditions in which the treatment must take place. This, for example, is the case in therapy for infective keratoconjunctivities, pink eye or IBK, an infection which usually affects cattle, sheep and goats. Presumably for these three species there are specific etiological factors and more particularly: in cattle the main microorganism involved seems to be Moraxella bovis (even though other agents of a viral origin should not be excluded, such as for example Rinotracheitis virus, in sheep Micoplasma, Rickettsiae and Clamidiae, and in goats Rickettsiae). The disease manifests itself in acute form and tends to spread rapidly: in the initial stages the symptomatology is characterized by blepharospasm and excessive lachrymtion, followed by purulent exudate, conjunctivities and keratitis, often accompanied by fever, loss of appetite and milk production. Particularly serious are the corneal lesions which in the final stages may even cause perforation of the cornea itself. The clinical progress of the disease varies from a few days to several weeks.

A vast selection of chemotherapeutic agents are used for treatment, administered both topically (often in association with steroid antiinflammatory agents), and systemic, including: tetracyclines, such as oxytetracycline, penicillins, such as cloxacillin and benzylpenicillin, sulfonamides, polymyxin B (associated with miconazole and prednisolone), chloramphenicol, tylosin and chloromycetin. Topical treatment of the disease, despite its apparent simplicity, is still an unsolved problem, since with the oculistic preparations used so far, it has not been possible for one reason or another, to obtain therapeutically efficient concentrations of antibiotics or sulphamides in the lachrymal secretion. This is quite understandable in the case of solutions, considering the mainly inclined position of the head in these animals, but the same is also true of semisolid medicaments, as the commonly used excipients do not possess the necessary qualities of adhesiveness to the corneal surface, since they do not usually have a high enought concentration of active substance and cannot achieve perfect distribution of the same (i.e., there is a presence of a distribution gradient). These defects of conventional colliriums in ophthalmic use have for example been described by Slatter et al., Austr. Vet. J., 1982, 59 (3), pp. 69–72.

With the esters of the present invention these difficulties can be overcome. The presence of the hyaluronic acid ester as a vehicle for ophthalmic drugs in fact allows the formulation of excellent preparations with no concentration gradients of the active substance and they are therefore perfectly homogenous, with perfect transparency and excellent adhesiveness to the corneal epithelium, with no sensitization effects, with excellent vehicling of the active substance and possibly a retard effect.

The above mentioned properties of the new medicaments may of course be exploited also in fields other than ophthalmology. They may be used in dermatology and in diseases of the mucous membranes, for example in the mouth. Furthermore, they may be used to obtain a systemic effect due to the effect of transcutaneous absorption, such as in suppositories. All these applications are possible both in human and veterinary medicine. In human medicine the new medicaments are particularly suitable for use in pediatrics. The present invention includes therefore in particular any of these therapeutic applications.

For the sake of brevity, from now on when the active substance of component (1) according to the invention is mentioned, it is to be understood to also include the association of one or more active substances.

The component (1) described above may first of all be defined in regard to its use in the various fields of therapy, starting with the distinction between human and veterinary medicine, and then specifying the various sectors of application with regard to the organs or tissues to be treated, such as, with reference to topical use, ophthalmology, dermatology, otorhinolaryngology, gynecology, angiology, neurology or any type of pathology of internal organs which may be treated with topical applications, for example with rectal applications.

The vehicling action of the hyaluronic esters also applies to associated medicaments of the type mentioned above in which the active substance acts not only topically or by nasal or rectal absorption, for example by nasal sprays or preparations for inhalation for the oral cavity or the pharynx, but also by oral or parenteral route, for example by intramuscular, subcutaneous or intravenous route, as it favors absorption of the drug into the application site. The new medicaments can therefore be applied, apart from in the fields already mentioned, in practically all sectors of medicine, such as internal medicine, for example in pathologies of the cardiovascular system, in infections of the respiratory system, the digestive system, the renal system, in diseases of an endocrinological nature, in oncology, in psychiatry etc., and may also be classified therefore from the point of view of their specific action, being perhaps anesthetics, analgesics, antiinflammatories, wound healers, antimicrobics, adrenergic agonists and antagonists, cytostatics, antirheumatics, antihypertensives, diuretics, sexual hormones, immunostimulants and immunosuppressants, for example, one of the drugs having the activity already described for the therapeutically active alcohols to be used as esterifying component according to the present invention, or for the therapeutically active bases used for the salification of the free carboxylic groups.

Component (1) of the above mentioned medicaments may also be, according to the invention, an association of two or more active substances, as contained in many known medicaments.

Regarding the field of ophthalmology, the indications may be for example: the miotic, antiinflammatory, wound healing and antimicrobial effects.

Examples of pharmacologically active substances to be used in ophthalmic medicaments according to the invention are: basic and non-basic antibiotics such as aminoglycosides, macrolides, tetracyclines and peptides, such as gentamycin, neomycin, streptomycin, dihydrostreptomycin, kanamycin, amikacin, tobramycin, spectinomycin, erythromycin, oleandomycin, carbomycin, spiramycin, oxytetracycline, rolitetracycline, bacitracin, polymyxin B. gramicidin, colistin, chlkoramphenicol, lincomycin, vancomycin, novobiocin, ristocetin, clindamycin, amphotericin B, griseofulvin, nystatin, and possibly their salts such as sulfate or nitrate, or associations of the same between themselves or with other active ingredients, such as those mentioned below.

Other ophthalmic drugs to be used to advantage according to the present invention are: other antiinfectives such as diethylcarbamazine, mebendazole, sulfamidics such as sulfacetamide, sulfadiazine, sulfisoxazole, antivirals and antitumorals such as iododeoxyuridine, adenine arabinoside, trifluorothymidine, acyclovir, ethyldeoxyuridine, bromovinyldeoxyuridine, 5-iodo-5'-amino-2',5'-dideoxyuridine; steroid antiinflammatories, such as dexamethasone, hydrocortisone, prednisolone, fluorometholone, medrysone and possibly their esters, for example phosphoric acid; non-steroid antiinflammatories such as indomethacin, oxyphenbutazone, flurbiprofen; wound healers such as epidermal growth factor, EGF; local anesthetics, such as Benoxinate, proparacaine and possibly their salts; cholinergic agonists such as pilocarpine, methcholine, carbomylcholine, aceclidine, physostigmine, neostigmine, demecarium and possibly their salts; cholinergic antagonist drugs such as atropine and their salts; adrenergic agonist drugs such as noradrenaline, adrenaline, naphazoline, methoxamine and possibly their salts; adrenergic antagonist drugs such as propanolol, timolol, pindolol, bupranolol, atenolol, metoprolol, oxprenolol, practolol, butoxamine, sotalol, butathrin, labetolol and possibly their salts.

Examples of the active substances to be used alone or in association among themselves or with other active principles in dermatology are: therapeutic agents as antiinfective agents, antibiotics, antimicrobials, antiinflammatory, cytostatic, cytotoxic, antiviral, anesthetic agents, and prophylactic agents, such a sun screens, deodorants, antiseptics and disinfectants. Of the antibiotics, particularly important are: erythromycin, bacitracin, gentamicin, neomycin, aureomicin, gramicidin and their associations, of the antibacterials and disinfectants: nitroflurzone, mafenide, chlorhexidine, and derivatives of 81-hydroxyquinoline and possibly their salts; of the antiinflammatory agents above all the corticosteroids such as prednisolone, dexamethazone, flumethasone, clobetasol, triamcinolone acetonide, betamethasone and their esters, such a valerates, benzoates, dipropionates; of the cytotoxic group,: fluorouracil, methotrexate, pdophyllin; of the anesthetics dibucaine, lidocain, benzocaine.

This list of course only gives some examples and any other agents described in the literature may be used.

As associations of drugs to be used in dermatology, the various antibiotics should be mentioned, such as erythromycin, gentamycin, neomycin, gramicidin, polymyxin B, among themselves, or associations of these antibiotics with antiinflammatory agents, for example corticosteroids, for example hydrocortisone+-neomycin, hydrocortisone+neomycin+polymyxin B+gramicidin, dexamethasone+neomycin, fluorometholone+neomycin, prednisolone+neomycin, triamcinolone+neomycin+gramicidin+nystatin, or any other association used in conventional preparations for dermatology.

The associations of various active substances are not of course limited to this field, but in each of the above mentioned sectors of medicine it is possible to use associations similar to those already in use for the known pharmaceutical preparations of the art.

In the above case of the use of a component (1) of a basic character, the salts which are formed with a partial hyaluronic ester (since the latter is used to excess) may be of various types, that is, all the remaining carboxylic groups may be salified or only an aliquot part, thereby producing esters—acid salts, or esters—neutral salts. The number of acid groups which are to be kept free may be of importance for the preparation of medicaments with a particular pH. Vice versa, it is possible to use an excess of basic component (1), in which case all the carboxylic groups available in the hyaluronic ester are salified with the base.

According to a particular aspect of the invention it is possible to prepare the medicaments of this type starting from previously isolated and possibly purified salts, in their solid anhydrous state, as amorphous powders, which form an aqueous solution on contact with the tissue to be treated, characterized by viscosity and elastic properties. These qualities are maintained even at stronger dilutions and it is possible therefore to use, in the place of the above mentioned anhydrous salts, more or less concentrated solutions in water or saline, possibly with the addition of other excipients or additives, such as for example other mineral salts to regulate the pH and osmotic pressure. It is of course possible to use the salts also for the preparation of gels, inserts, creams or ointments, containing also other excipients or ingredients used in traditional formulations of these pharmaceutical preparations.

According to a major aspect of the invention however, the medicaments containing the hyaluronic ester or their salts with therapeutically active or inactive substances as a vehicle are used alone (except possibly with an aqueous solvent). Also included in the invention are the mixtures obtainable from all the types of medicaments described here, mixtures of the same medicaments, and also possibly mixtures of the new hyaluronic esters with free hyaluronic acid or mixtures of their salts, for example sodium salts.

Component (1) according to the invention may also be associations or mixtures of two or more such drugs and possibly also with other principles. For example, in ophthalmology, a drug may be associated with an antibiotic or antiphlogistic substance and a vasoconstrictor or with several antibiotics, one or more antiphlogistic substances, or with one or more antibiotics, a mydiatric or a miotic or wound healing or antiallergic agent, etc. For example the following associations of ophthalmic drugs may be used: kanamycin phenylephrine+dexamethasone phosphate; kanamycin+betamethasone phosphate+phenylephrine; or similar associations with other antibiotics used in ophthalmology, such as rolitetracycline, neomycin, gentamicin, tetracycline.

If in the place of just one active substance component (1), associations of active substances are used, such as those mentioned above, the salts of the basic active substances and the partial ester of hyaluronic acid may be mixed salts of one or more of such basic substances or possibly mixed salts of this type with a certain number of other acid groups of the polysaccharides salified with metals or bases mentioned above. For example, it is possible to prepare salts of a partial ester of hyaluronic acid or of one of the molecular fractions Hyalastine or Hyalectin with a pharmacologically inactive alcohol, for example a lower alkanol and with a certain percentage of salified acid groups with the antibiotic kanamycin, another percentage of carboxylic groups salified with the vasoconstrictor phenylephrine, and a remaining percentage of acid groups may be, for example, free of salified with sodium or one of the other above mentioned metals. It is also possible to mix this type of mixed salt with free hyaluronic acid or its fractions or their metallic salts, as indicated above for the medicaments containing salts of one single active substance with the aforementioned polysaccharide esters.

Of the examples discussed for ophthalmology and dermatology it is possible to understand by analogy which medicaments according to the present invention are to be used in the above mentioned fields of medicine, such as for example in otorhinolaryngology, odontology or in internal medicine, for example in endocrinology. Such preparations may, therefore, be for example antiinflammatories, vasoconstrictors, or vasocompressors such as those already mentioned for ophthalmology, vitamins, antibiotics, such as those mentioned above, hormones, chemiotherapics, antibacterials, etc. also as mentioned above for use in dermatology.

The associated medicaments of a hyaluronic ester with a pharmacologically active substance may contain other pharmaceutical vehicles, such as those mentioned below for the pharmaceutical preparations containing only hyaluronic esters, and may appear in the form of ointments, creams, pastilles, gelatine capsules, capsules, aqueous or oily solutions, sprays, suppositories, etc. However, according to a particular aspect of the present invention it is preferable to use medicaments containing an association of components (1) and (2), with component (2) as the sole vehicle (apart from a possible solvent such as an aqueous solvent).

Of the medicaments of the invention the following are of particular importance, according to each case, those with a degree of acidity suitable for the environment to which they are to be applied, that is with a physiologically tolerable pH. The adjustment of the pH, for example in the above mentioned salts of the partial ester of hyaluronic acid with a basic active substance, may be done by suitably regulating the quantities of polysaccharide, of its salts and of the basic substance itself. Thus, for example, if the aciditiy of a salt of the partial ester of hyaluronic acid with a basic substance is too high, the excess of free acid groups cans be neutralized with the above mentioned inorganic bases, for example with the hydrate of sodium or potassium or ammonium.

Method of Preparing HY Esters of the Invention

Method A

The esters of hyaluronic acid according to the invention may be prepared by methods known per se for the esterification of carboxylic acids, for example by treatment of free hyaluronic acid with the desired alcohols in the presence of catalyzing substances, such as strong inorganic acids or ionic exchangers of the acid type, or with an etherifying agent capable of introducing the desired alcoholic residue in the presence of inorganic or organic bases. As etherifying agents it is possible to use those known in literature, such as especially the esters of various inorganic acids or of organic sulphonic acids, such as hydracids, that is hydrocarbyl halogenides, such as methyl or ethyl iodide, or neutral sulphates or hydrocarbyl acids, alfites, carbonates, silicates, phosphites or hydrocarbyl sulfonates, such as methyl benzene or p-toluenesulfonate or methyl or ethyl chlorosulfonate. The reaction may take place in a suitable solvent, for example an alcohol, preferably that corresponding to the alkyl group to be introduced in the carboxyl group. But the reaction may also take place in non-polar solvents, such as ketones, ethers, such as dioxane or aprotic solvents, such as dimethylsulphoxide. As a base it is possible to use for example a hydrate of an alkaline or alkaline earth metal or magnesium or silver oxide or a basic salt or one of these metals, such as a carbonate, and, of the organic bases, a tertiary azotized base, such as pyridine or collidine. In the place of the base it is also possible to use an ionic exchanger of the basic type.

Another esterification method employs the metal salts or salts with organic azotized bases, for example ammonium or ammonium substitute salts. Preferably, the salts of the alkaline or alkaline earth metals are used, but also any other metallic salt may be used. The esterifying agents are also in this case those mentioned above and the same applies to the solvents. It is preferable to use aprotic solvents, for example dimethylsulphoxide and dimethylformamide.

In the esters obtained according to this procedure or according to the other procedure described hereafter, free carboxylic groups of the partial esters may be salified, if desired, in a per se known manner.

Method B

The hyaluronic esters of the present invention may, however, be prepared to advantage according to a second method which may be generally applied to the preparation of carboxylic esters of acidic polysaccharides with carboxyl groups. This method consists of treating a quaternary ammoniuim salt of an acidic polysaccharide containing carboxyl groups with an etherifying agent, preferably in an aprotic organic solvent. As starting acidic polysaccharides it is possible to use, for example, apart from hyaluronic acid, other acidic polysacchariddes of animal or vegetable origin and synthetically modified derivatives of the same, such as acid hemicellulose, obtainable from the alkaline extracts of certain plants and after precipitation of xylans, whose disaccharide components are made up of D-glucuronic acid and D-xylopyranose, (see "The Carbohydrates" by W. Pigman, pages 668–669—R. L. Whistler, W. M. Corbett), the pectins and acidic polysaccharides obtainable from the same, that is, galacturonan, acaidic polysaccharides obtainable from plant gum (exudates), such as arabic gum, tragacanth, and finally acidic polysaccharides derived from seaweed, such as agar and carrageenans. As starting material it is of course possible to use also the molecular fractions obtained by degradation of all of the above mentioned polysacchaarides.

As organic solvents it is preferable to use aprotic solvents, such as dialkylsulphoxides, dialkylcarboxamides, such as in particular lower alkyl dialkylsulphoxides, especially dimethylsulphoxide, and lower alkyl dialkylamides of lower aliphatic acids, such as dimethyl or diethylformamide or dimethyl or diethylacetamide.

Other solvents however are to be considered which are not always aprotic, such as alcohols, ethers, ketones, esters, especially aliphatic or heterocyclic alcohols and ketones with a lower boiling point, such as hexafluoro isopropanol, trifluoroethanol, and N-methylpyrrolidone.

The reaction is effected preferably at a temperature range of between about 0° C. and 100° C., especially between about 25° C. and 75° C., for example at about 30° C.

The esterification is carried out preferably by adding by degrees the esterifying agent to the above mentioned ammonium salt to one of the above mentioned solvents, for example to dimethylsulphoxide.

As an alkylating agent it is possible to use those mentioned above, especially the hydrocarbyl halogens, for example alkyl halogens. As starting quaternary ammonium salts it is preferable to use the lower ammonium tetraalkylates, with alkyl groups preferably between 1 and 6 carbon atoms. Mostly, hyaluronate of tetrabutylammonium is used. It is possible to prepare these quaternary ammonium salts by reacting a metallic salt of acidic polysaccharide, preferably one of those mentioned above, especially sodium or potassium salt, in aqueous solution with a salified sulphonic resin with a quaternary ammonium base.

The tetraalkylammonium salt of the acidic polysaccharide can be obtained by freeze drying the eluate. The tetraalkylammonium salts of acidic polysaccharides used as starting compounds of the new procedure and deriving from inferior alkyls, especially alkyls with between 1 and 6 carbon atoms, are new and form another object of the present invention. Surprisingly, such salts have provided to be soluble in the above mentioned organic solvents, and for this reason the esterification of acidic polysaccharide according to the above mentioned procedure B is particularly easy and gives generous yields. It is therefore only by using this kind of procedure that one can exactly dose the number of carboxylic groups of acidic polysaccharide which are to be esterified.

The new procedure B is very suitable especially for the preparation of hyaluronic esters according to the present invention. In particular, therefore, as starting compounds of the new procedure, the quaternary ammonium salts of hyaluronic acid, especially those deriving from lower alkyls, and especially from alkyls with between 1 and 6 carbon atoms, are new and form a particular object of the present invention.

One variation of the previously described procedure consists in reacting potassium salt or acidic polysaccharide sodium, suspended in a suitable solution such as dimethylsulphoxide, with a suitable alkylating agent in the presence of catalytic quantities of a quaternary ammonium salt, such as iodide of tetrabutylammonium.

For the preparation of the new esters according to the present invention it is possible to use hyaluronic acids of any origin, such as for example the acids extracted from the above mentioned natural starting materials, for example from cocks' combs. The preparation of such acids is described in literature: preferably, purified hyaluronic acids are used. According to the invention, especially used are hyaluronic acids comprising molecular fractions of the integral acids obtained directly by extraction of the organic materials with molecular weights varying within a wide range, for example from about 90%–80% (MW=11.7–10.4 million) to 0.2% (MW 30,000) of the molecular weight of the integral acid having a molecular weight of 13 million, preferably between 5% and 0.2%. Such fractions may be obtained with various procedures described in literature, such as by hydrolyzing, oxydizing, enzymatic or physical procedures, such as mechanical or radiational procedures. Primordial extracts are therefore often formed during these same purification procedures (for example see the article by Balazs et al. quoted above in "Cosmetics & Toiletries"). The separation and purification of the molecular fractions obtained are brought about by known techniques, for example by molecular filtration.

One fraction of purified HY suitable for use according to the invention is for example that known as "non-inflammatory-NIF-NaHA sodium hyaluronate described by Balazs in the booklet "Healon"—A guide to its use in Ophthalmic Surgery D. Miller & R. Stegmann, eds. John Wiley & Sons N.Y. 81983: p. 5.

Particularly important as starting materials for the esters of the present invention are two purified fractions obtainable from hyaluronic acid, for example the ones extracted from cocks' combs, known as "Hyalastine"

and "Hyalectin". The fraction Hyalastine has an average molecular weight of about 50,000 to 100,000 while the fraction Hyalectin has an average molecular weight of between about 500,000 and 730,000. A combined fraction of these two fractions has also been isolated and characterized as having an average molecular weight of about 250,000 to about 350,000. This combined fraction may be obtained with a yield of 80% of total hyaluronic acid available in the particular starting material, while the fraction Hyalectin may be obtained with a yield of 30% and the fraction Hyalastine with a yield of 50% of the starting HY. The preparation of these fractions is described in the Examples A–C.

The salification of HY with the above metals, for the preparation of starting salts for the particular esterification procedure of the present invention described above, is performed in a per se known manner, for example by reacting HY with the calculated base quantity, for example with alkaline hydrates or with basic salts of such metals, such as carbonates or bicarbonates.

In the partial esters of the present invention it is possible to salify all the remaining carboxylic groups or only part of them, dosing the base quantities so as to obtain the desired stoichiometric degree of salification. With the correct degree of salification it is possible to obtain esters with a wide range of different dissocation constants and which therefore give the desired pH, in solution or "in situ" at the time of therapeutic application.

Of the new products of the present invention, of particular importance are the esters and their salts described above and those described in the following illustrative Examples.

The present invention also includes modifications of the preparation procedures of the new esters and their salts, in which a procedure is interrupted at any given stage or started with an intermediate compound on which the remaining stages are carried out, or in which the starting products are formed in situ.

The invention is illustrated by the following Examples which are not intended to be limitive of the invention.

PREPARATION EXAMPLES

The following Examples A–C describe the procedures for preparing the preferred hyaluronic acids fractions utilized in the present invention.

EXAMPLE A

Method for obtaining a mixture of Hyalastine and Hyalectin fractions having no inflammatory activity Fresh or frozen cocks' combs, (3000 g) are minced in a meat mincer and then carefully homogenized in a mechanical homogenizer. The paste thus obtained is placed in a stainless steel container AISI 316 or in glass and treated with 10 volumes of anhydrous acetone. The whole is agitated for 6 hours at a speed of 50 rpm. It is left to separate for 12 hours and the acetone is discarded by syphoning. The acetone extraction is repeated until the discarded acetone has reached the correct degree of humidity (Karl-Fischer method). The whole is then centrifuged and vacuum dried at a suitable temperature for 5–8 hours. In this way about 500–600 g of dry powdered cocks' combs are obtained.

300 gr. of dry powder are exposed to enzymatic digestion with papain (0.2 g) in aqueous conditions, buffered with phosphate buffer in the presence of a suitable quantity of hydrochloride cysteine. The resultant is agitated for 24 hours at 60 rpm keeping the temperature constant at 60°–65° C. It is then cooled at 25° C. and Celite ® (60 gr) is added maintaining the agitation for another hour. The resulting mixture is filtered until a clear liquid is obtained. The clear liquid then undergoes molecular ultrafiltration using membranes with a molecular exclusion limit of 30,000 in order to retain on the membrane those molecules with a molecular weight greater than 30,000.

The product is ultrafiltered from 5 to 6 original volumes adding distilled water continually to the product in ultrafiltration. The addition of water is suspended and the ultrafiltration is continued until the volume is reduced to ⅓ of the original volume.

The residue liquid is rendered 0.1M by the addition of sodium chloride and the temperature is brought to 50° C. Under agitation at 60 rpm, 45 g of cetylpyridinium chloride are added. It is agitated for 60 minutes and then 50 g of Celite ® are added. Under agitation, the temperature of the whole is brought to 25° C. and the precipitate formed by centrifugation is gathered. The precipitate obtained is suspended in a 0.01M solution in sodium chloride (5 liters) containing 0.05% of cetylpiridinium chloride. The resulting suspension is agitated for 60 minutes at 50° C.; the temperature is then brought to 25° C. and the precipitate is centrifuged. The washing operation is repeated 3 times after which the precipitate is gathered in a receptacle containing 3 liters of a 0.05M solution of sodium chloride containing 0.05% of cetylpyridinium chloride. It is agitated at 60 rpm for 60 minutes and the temperature is kept constant at 25° C. for two hours. The supernatant is eliminated by centrifugation. The procedure is repeated several times with solutions of 0.1M sodium chloride containing 0.05% of cetylpyridinium chloride. The mixture is centrifuged and the supernatant is discarded. The precipitate is dispersed in a solution of 0.30M sodium chloride containing 0.05% of cetylpyridinium chloride (3 liters). The mixture is agitated and both the precipitate and the clear liquid are gathered. Extraction is repeated three more times on the precipitate, each time using 0.5 liter of the same aqueous solution.

Finally the precipitate residue is eliminated and the clear liquids are all placed together in a single container. The temperature of the liquid is brought to 50° C. under constant agitation. The liquid is then brought to 0.23M with sodium chloride. 1 gr of cetylpyridinium chloride is added, and it is maintained in agitation for 12 hours.

The mixture is cooled at 25° C. and then filtered first on Celite ® pack and then through a filter. It then undergoes molecular ultrafiltration again, on a membrane with a molecular exclusion limit of 30,000 ultrafiltering three initial volumes with the addition of a solution of 0.33M sodium chloride. The addition of sodium chloride solution is interrupted and the volume is reduced to ¼ of the initial volume. The solution thus concentrated is precipitated under agitation (60 rpm) at 25° C. with 3 volumes of ethanol (95%). The precipitate is gathered by centrifugation and the supernatant is discarded. The precipitate is dissolved in 1 lt of 0.01M solution in sodium chloride and the precipitation is repeated with 3 volumes of ethanol 95%.

The precipitate is gathered and washed first with 75% ethanol (3 times), then with absolute ethanol (3 times), and lastly with absolute acetone (3 times).

The product thus obtained (HYALASTINE+HYALECTIN fractions) has an average molecular weight of between 250,000 and 350,000.

The yield of HY is 0.6% of the original fresh tissue.

EXAMPLE B

Method for obtaining the fraction Hyalastine from the mixture obtained by the method described in Example A The mixture obtained by the method described in Example A is dissolved in twice distilled apyrogenetic water at the rate of 10 mg of product to each 1 ml of water. The solution obtained is exposed to molecular filtration through filter membranes with a molecular exclusion limit of 200,000, following a concentration technique on the membrane without the addition of water. During the ultrafiltration process through membranes with a molecular exclusion limit of 200,000, the molecules with a molecular weight of more than 200,000 do not pass through, while the smaller molecules pass through the membrane together with the water. During the filtration procedure no water is added, so that the volume decreases, and there is therefore an increase in the concentration of molecules with a molecular weight of more than 200,000. The product is ultrafiltered until the volume on top of the membrane is reduced to 10% of the initial volume. Two volumes of apyrogenetic twice distilled water are added and it is then ultrafiltered again until the volume is reduced to ⅓. The operation is repeated twice more. The solution passed through the membrane is brought to 0.1M with sodium chloride and then precipitated with 4 volumes of ethanol at 95%. The precipitate is washed 3 times with ethanol at 75% and then vacuum dried.

The product thus obtained (HYALASTINE fraction) has an average molecular weight of between 50,000 and 100,000. The yield of HY is equal to 0.4% of the original fresh tissue.

EXAMPLE C

Method of obtaining the fraction Hyalectin

The concentrated solution gathered in the container on top of the ultrafiltration membrane with a molecular exclusion of 200,000 as in Example B, is diluted with water until a solution containing 5 mg/ml of hyaluronic acid is obtained, as determined by quantitative analysis based on the dosage of glucuronic acid.

The solution is brought to 0.1M in sodium chloride and then precipitated with 4 volumes of ethanol at 95%. The precipitate is washed 3 times with ethanol at 75% and then vacuum dried.

The product thus obtained (HYALECTIN fraction) has an average molecular weight of between 500,000 and 730,000. This corresponds to a specific fraction of hyaluronic acid with a defined length of molecular chain of about 2,500 to 3,500 saccharide units with a high degree of purity. The yield of HY is equal to 0.2% of the original fresh tissue.

EXAMPLE D

Preparation of the salt of tetrabutylammonium of hyaluronic acid (HY)

4.02 g of HY sodium salt (10 m.Eq.) are solubilized in 400 ml of distilled $H_2O$. The solution is then eluted in a thermostatic column at 4° C. containing 15 ml of sulphonic resin (Dowex 50×8) in Tetrabutylammonium form. The eluate, free from sodium, is instantly frozen and freeze-dried. Yield: 6.18 g.

EXAMPLE 1

Preparation of the (partial) propyl ester of hyaluronic acid (HY)

50% of the esterified carboxylic groups
50% of the salified carboxylic groups (Na)

12.4 g of HY tetrabutylammonium salt with a molecular weight 170,000 corresponding to 20 m.Eq. of a monomeric unit are solubilized in 620 ml of dimethylsulfoxide at 25° C., 1.8 g (10.6 m.Eq.) of propyl iodide are added and the resulting solution is kept at a temperature of 30° for 12 hours.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30°.

The product is then dissolved in 550 ml of water containing 1% of sodium chloride and the solution is slowly poured into 3,000 ml of acetone under constant agitation. A precipitate is formed which is filtered and washed twice with 500 ml of acetone/water (5:1) and three times with 500 ml of acetone and finally vacuum dried for 24 hours at 30°. 7.9 g of the partial propyl ester compound in the title are obtained. Quantitative determination of the ester groups is carried out using the method of R. H. Cundiff and P. C. Markunas [Anal. Chem. 33, 1028–1030, (1961)].

EXAMPLE 2

Preparation of the (partial) isopropyl ester of hyaluronic acid (HY)

50% of esterified carobyxlic groups
50% of salified carboyxlic groups (Na)

12.4 g of HY tetrabutylammonium salt with a molecular weight of 160,000 corresponding to 20 m.Eq. of a monomeric unit are solubilized in 620 ml of dimethysulfoxide at 25°, 1.8 g (10.6 m.Eq.) of isopropyl iodide are added and the resulting solution is kept for 12 hours at 3020 .

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30°.

The produce is then dissolved in 500 ml of water containing 1% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30°. 7.8 g of the partial isopropyl ester compound in the title are obtained. Quantitative determination of the ester groups is carried out using the method of R. H. Cundiff and P.C. Markunas [Anal. Chem. 33, 1028–1030, (1961)].

EXAMPLE 3

Preparation of the (partial) ethyl ester of hyaluronic acid (HY)

75% of esterified carboxylic groups
25% of salified carobyxlic groups (Na)

12.4 g of HY tetrabutylammonium salt with a molecular weight of 250,000 corresponding to 20 m.Eq. of a monomeric unit are solubilized in 620 ml of dimethysulfoxide at 25°, 2.5 g (15.9 m.Eq.) of ethyl iodide are added and the resulting solution is kept for 12 hours at 30°.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30°.

The produce is then dissolved in 500 ml of water containing 1% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30°. 7.9 g of the partial ethyl ester compound in the title are obtained. Quantitative determination of the ester groups is carried out using the method of R. H. Cundiff and P. C. Markunas [Anal. Chem. 33, 1028-1030, (1961)].

EXAMPLE 4

Preparation of the (partial) methyl ester of hyaluronic acid (HY)

75% of esterified carboxylic groups
25% of salified carboxylic groups (Na)

12.4 g of HY tetrabutylammonium salt with a molecular weight of 80,000 corresponding to 20 m.Eq. of a monomeric unit are solubilized in 620 ml of dimethylsulfoxide at 25°, 2.26 g (15.9 m.Eq.) of methyl iodide are added and the resulting solution is kept for 12 hours at 30°.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30°.

The product is then dissolved in 550 ml of water containing 1% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30°. 7.8 g of the partial methyl ester compound in the title are obtained. Quantitative determination of the ester groups is carried out using the method of R. H. Cundiff and P. C. Markunas [Anal. Chem. 33. 1028-1030, (1961)].

EXAMPLE 5

Preparation of the methyl ester of hyaluronic acid (HY)

12.4 g of HY tetrabutylammonium salt with a molecular weight of 120,000 corresponding to 20 m.Eq. of a monomeric unit are solubilized in 620 ml of dimethylsulfoxide at 25°, 3 g (21.2 m.Eq.) of methyl iodide are added and the solution is kept for 12 hours at 30°.

The resulting mixture is slowly poured into 3,500 ml of ethyl acetate under constant agitation. A precipitate is formed which is filtered and washed four times with 500 ml of ethyl acetate and finally vacuum dried for twenty four hours at 30°.

8 g of the ethyl ester product in the title are obtained. Quantitative determination of the ester groups is carried out using the method of R. H. Cundiff and P. C. Markunas [Anal. Chem. 33, 1028-1030, (1961)].

EXAMPLE 6

Preparation of the ethyl ester of hyaluronic acid (HY)

12.4 g of HY tetrabutylammonium salt with a molecular weight of 85,000 corresponding to 20 m.Eq. of a monomeric unit are solubized in 620 ml of dimethylsulfoxide at 25°, 3.3 g (21.2 m.Eq.) of ethyl iodide are added and the solution is kept for 12 hours at 30°.

The resulting mixture is slowly poured into 3,500 ml of ethyl acetate under constant agitation. A precipitate is formed which is filtered and washed four times with 500 ml of ethyl acetate and finally vacuum dried for twenty-four hours at 30°.

8 g of the ethyl ester product in the title are obtained. Quantitative determination of the ester groups is carried out using the method of R. H. Cundiff and P. C. Markunas [Anal. Chem. 33, 1028-1030, (1961)].

EXAMPLE 7

Preparation of the propyl ester of hyaluronic acid (HY)

12.4 g of HY tetrabutylammonium salt with a molecular weight of 170,000 corresponding to 20 m.Eq. of a monomeric unit are solubilized in 620 ml of dimethylsulfoxide at 25°, 3.6 g (21.2 m.Eq.) of propyl iodide are added and the solution is kept for 12 hours at 30°.

The resulting mixture is slowly poured into 3,500 ml of ethyl acetate under constant agitation. A precipitate is formed which is filtered and washed four times with 500 ml of ethyl acetate and finally vacuum dried for twenty-four hours at 30°.

8.3 g of the propyl ester product in the title are obtained. Quantitative determination of the ester groups is carried out using the method of R. H. Cundiff and P. C. Markunas [Anal. Chem. 33, 1028-1030, (1961)].

EXAMPLE 8

Preparation of the (partial) butyl ester of hyaluronic acid (HY)

50% of esterified carboxylic groups
50% of salified carboxylic groups (Na).

12.4 g of HY tetrabutylammonium salt with a molecular weight of 620,000 corresponding to 20 m.Eq. of a monomeric unit are solubilized in 620 ml of dimethylsulfoxide at 25°, 1.95 g (10.6 m.Eq.) of n-butyl iodide are added and the resulting solution is kept for 12 hours at 30°.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30°.

The product is then dissolved in 550 ml of water containing 1% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30°. 8 g of the partial butyl ester compound in the title are obtained. Quantitative determination of the ester groups is carried out using the method of R. H. Cundiff and P. C. Markunas [Anal. Chem. 33, 1028–1030, (1961)].

EXAMPLE 9

Preparation of the (partial) ethoxycarbonylmethyl ester or hyaluronic acid (HY)

75% of esterified carobyxlic groups
25% of salified carboxylic groups (Na)

12.4 g of HY tetrabutylammonium salt with a molecular weight of 180,000 corresponding to 20 m.Eq. of a monomeric unit are solubilized in 620 ml of dimethylsulfoxide at 25°, 2 g of tetrabutylammonium iodide and 1.84 g (15 m.Eq.) of ethyl chloroacetate are added and the resulting solution of kept for 24 hours at 30°.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30° C.

The product is then dissolved in 550 ml of water containing 1% of sodium chloride and the solution is slowly poured into 3,000 ml of acetone under constant agitation. A precipitate is formed which is filtered and washed twice with 500 ml of acetone/water 5:1 and three times with 500 ml di acetone and finally vacuum dried for 24 hours at 30°. 10 g of the partial ethoxycarbonyl methyl ester compound in the title are obtained. Quantitative determination of the ethoxylic ester groups is carried out using the method of R. H. Cundiff and P. C. Markunas [Anal. Chem. 33, 1028–1030, (1961)].

EXAMPLE 10

Preparation of the (partial) cortisone ester ($C_{21}$) of hyaluronic acid (HY)

20% of esterified carboxylic groups
80% of salified carboxylic groups (Na)

6.2 g of HY tetrabutylammonium salt with a molecular weight of 105,000 corresponding to 10 m.Eq. of a monomeric unit are solubilized in 310 ml of dimethylsulfoxide at 25°, 0.850 g (2 m.Eq.) of 21-bromo-4-pregnene-17 α-ol-3, 11, 20-trione are added and the resulting solution is kept for 24 hours at 30°.

A solution containing 100 ml of water and 5 g of sodium chloride is added and the resulting mixture is slowly poured into 2,000 ml of acetone under constant agitation. A precipitate is formed which filtered and washed three times with 100 ml of acetone/water 5:1 and three times with acetone and finally vacuum dried for eight hours at 30°.

The product is then dissolved in 300 ml of water containing 1% of sodium chloride and the solution is slowly poured into 1,500 ml of acetone under constant agitation. A precipitate is formed which is filtered and washed twice with 100 ml of acetone/water 5:1 and three times with 100 ml of acetone and finally vacuum dried for 24 hours at 30°. 4.5 g of the partial cortisone ester compound in the title are obtained. Quantitative determination of cortisone, after mild alkaline hydrolysis with a hydroalcoholic solution of $Na_2CO_3$ and extraction with chloroform, is carried out according to British Pharmacopea, 1980, p. 127.

EXAMPLE 11

Preparation of the (partial) hydrocortisone ester ($C_{21}$) of hyaluronic acid (HY)

20% of esterified carboxylic groups
80% of salified carboxylic groups (Na).

6.2 g of HY tetrabutylammonium salt with a molecular weight of 80,000 corresponding to 20 m.Eq. of a monomeric unit are solublized in 310 ml of dimethylsulfoxide at 25°, 0.850 g (2 m.Eq.) of 21-bromo-4-pregnene-11β, 17 α-diol-3,20-dione are added and the resulting solution is kept for 24 hours at 30°.

A solution is then added containing 100 ml of water and 5 g of sodium chloride and the resulting mixture is slowly poured into 2,000 ml of acetone under constant agitation. A precipitate is formed which is filtered and washed three times with 100 ml of acetone/water 5:1 and three times with acetone and finally vacuum dried for eight hours at 30°.

The product is then dissolved in 300 ml of water containing 1% of sodium chloride and the solution is slowly poured into 1,500 ml of acetone under constant agitation. A precipitate is formed which is filtered and washed twice with 100 ml of acetone/water 5:1 and three times with 100 ml of acetone and finally vacuum dried for 24 hours at 30°. 4.4 g of the partial hydrocortisone ester compound in the title are obtained. Quantitative determination of hydrocortisone, after mild alkaline hydrolysis with hydroalcoholic solution of $Na_2CO_3$ and extraction with chloroform, is carried out according to British Pharmacopea, 1980, p. 224.

EXAMPLE 12

Preparation of the (partial) fluorocortisone ester ($C_{21}$) of hyaluronic acid (HY)

20% of esterified carboxylic groups
80% of salified carboxylic groups (Na)

6.2 g of HY tetrabutylammonium salt with a molecular weight of 80,000 corresponding to 10 m.Eq. of a monomeric unit are solubilized in 310 ml of dimethylsulfoxide at 25°, 0.89 g (2 m.Eq.) of 9-fluoro-21-bromo-4-pregnene-11β, 17 α-diol-3,20-dione are added and the resulting solution is kept for 12 hours at 30°.

A solution is then added containing 62 ml of water and 5 g of sodium chloride and the resulting mixture is slowly poured into 2,000 ml of acetone under constant agitation. A precipitate is formed which is filtered and washed three times with 100 ml of acetone/water 5:1 and three times with acetone and finally vacuum dried for eight hours at 30°.

The product is then dissolved in 300 ml of water containing 1% of sodium chloride and the solution is slowly poured into 1,500 ml of acetone under constant agitation. A precipitate is formed which is filtered and washed twice with 100 ml of acetone/water 5:1 and three times with 100 ml of acetone and finally vacuum dried for 24 hours at 30°. 4.6 g of the partial fluorocortisone compound in the title are obtained. Quantitative

EXAMPLE 13

Preparation of the (partial) desoxycorticosterone ester ($C_{21}$) of hyaluronic acid (HY)

20% of esterified carboxylic groups
80% of salified carboxylic groups (Na)

6.21 g of HY tetrabutylammonium salt with a molecular wieght of 105,000 corresponding to 10 m.Eq. of a monomeric unit are solubilized in 310 ml of dimethylsulfoxide at 25°, 0.661 g (2 m.Eq.) of 21-bromo-4-pregnene-3, 20-dione are added and the resulting solution is kept for 24 hours at 30°.

A solution is then added containing 100 ml of water and 5 g of sodium chloride and the resulting mixture is slowly poured into 2,000 ml of acetone under constant agitation. A precipitate is formed which is filtered and washed three times with 100 ml of acetone/water 5:1 and three times with acetone and finally vacuum dried for eight hours at 30°.

The product is then dissolved in 300 ml of water containing 1% of sodium chloride and the solution is slowly poured into 1,500 ml of acetone under constant agitation. A precipitate is formed which is filtered and washed twice with 100 ml of acetone/water 5:1 and three times with 100 ml of acetone and finally vacuum dried for 24 hours at 30°. 4.5 g of the partial desoxycorticosterone ester compound in the title are obtained. Quantitative determination of desoxycorticosterone, after mild alkaline hydrolysis with hydroalcoholic solution of $Na_2CO_3$ and extraction with chloroform, is carried out according to British Pharmacopea, 1980, p. 137.

EXAMPLE 14

Preparation of the (mixed ethanol and cortisone ester ($C_{21}$) of hyaluronic acid (HY)

80% of the carboxylic groups esterified with ethanol
20% of the carboxvlic groups esterified with cortisone ($C_{21}$).

6.2 g of HY tetrabutylammonium salt with a molecular weight of 70,000 corresponding to 10 m.Eq. of a monomeric unit are solublized in 310 ml of dimethylsulfoxide at 25°, 1.25 g (8 m.Eq.) of ethyl iodide are added and the resulting solution is kept for 12 hours at 30°.

0.85 g (2 m.Eq.) of 21-bromo-4-pregnene-17 α-ol-3, 11, 20-trione are added and the solution is kept for 24 hours at 30°.

A solution is then added containing 100 ml of water and 5 g of sodium chloride and the resulting mixture is slowly pourd into 2,000 ml of acetone under constant agitation. A precipitate is formed which is then filtered and washed three times with 100 ml of acetone/water 5:1 and three times with 100 ml of acetone and finally vacuum dried for eight hours at 30°.

4.6 g of the mixed ethanol and cortisone ester compound in the title are obtained. Quantitative determination of cortisone, after mild alkaline hydrolysis is with hydroalcoholic solution of $Na_2CO_3$ and extraction with chloroform, is carried out according to British Pharmacopea, 1980.

Quantitative determination of the ethoxyls is carried out according to R. H. Cundif and P. C. Markunas Anal. Chem. 33, 1028–1030 (1961)].

EXAMPLE 15

Preparation of the (mixed) ethanol and hydrocortisone ester ($C_{21}$) of hyaluronic acid (HY)

80% of carboxvlic groups esterified with ethanol
20% of carboxylic groups esterified with hydrocortisone ($LC_{21}$)

6.2 g of HY tetrabutylammonium salt with a molecular weight of 125,000 corresponding to 10 m.Eq. of a monomeric unit are solubilized in 310 ml of dimethylsulfoxide at 25°, 1.25 g M.Eq.) of ethyl iodide are added and the solution is kept at 30° for 12 hours.

0.85 g (2 m.Eq.) of 21-bromo-4-pregnene-11β, 17 α-diol-3,20-dione are added and the solution is kept for 24 hours at 30°.

A solution is then added containing 100 ml of water and 5 g of sodium chloride and the resulting mixture is slowly poured into 2,000 ml of acetone under constant agitation. A precipitate is formed which is filtered and washed three times with 100 ml of acetone/water 5:1 and three times with 100 ml of acetone and finally vacuum dried for eight hours at 30°.

4.6 g of the mixed ethanol and hydrocortisone ester compound in the title are obtained. Quantitative determination of hydrocortisone, after mild alkaline hydrolysis with hydroalcoholic solution of $Na_2CO_3$ and extraction with chloroform, is carried out according to British Pharmacopea, 1980.

Quantitative determination of the ethoxyls is carried out according to R. H. Cundiff and P. C. Markunas [Anal. Chem. 33, 1028–1030 (1961)].

EXAMPLE 16

Preparation of the (mixed) ethanol and fluorocortisone ester ($C_{21}$) of hyaluronic acid (HY)

80% of carboxylic groups eserified with ethanol
20% of carboxylic groups esterified with fluorocortisone ($C_{21}$).

6.2 g of HY tetrabutylammonium salt with a molecular weight of 70,000 corresponding to 10 m.Eq. of a monomeric unit are solubilized in 310 ml of dimethylsulfoxide at 25°, 1.25 g (8 m.Eq.) of ethyl iodide are added and the solution is kept for 24 hours at 30°.

0.89 g (2 m.Eq.) of 9 α-fluoro-21-bromo-4-pregnene-11 β, 17 α-diol-3,20-dione are added and the solution is kept for 24 hours at 30°.

A solution is then added containing 100 ml of water and 5 g of sodium chloride and the resulting mixture is slowly poured into 2,000 ml of acetone under constant agitation. A precipitate is formed which is filtered and washed three times with 100 ml of acetone/water 5:1 and three times with 100 ml of acetone and finally vacuum dried for eight hours at 30°.

4.6 g of the mixed ethanol and fluorocortisone ester compound featured in the title are obtained. Quantitative determination of fluorocortisone, after mild alkaline hydrolysis with hydroalcoholic solution of $Na_2CO_3$ and extraction with chloroform, is carried out according to British Pharmacopea, 1980.

Quantitative determination of the ethoxyls is carried out according to R. H. Cundiff and P. C. Markunas [Anal. Chem. 33, 1028–1030 (1961)].

EXAMPLE 17

Preparation of the (mixed) ethanol and desoxycorticosterone ester ($C_{21}$) of hyaluronic acid (HY)

80% of carboxylic groups esterified with ethanol
20% of carboxylic groups esterified with desoxycorticosterone ($C_{21}$)

6.2 g of HY tetrabutylammonium salt with a molecular weight of 70,000 corresponding to 10 m.Eq. of a monomeric unit are solubilized in 310 ml of dimethylsulfoxide at 25°, 1.25 g (8 m.Eq.) of ethyl iodide are added and the resulting solution is kept for 12 hours at 30°.

0.661 g (2 m.Eq.) of 21-bromo-4-pregnene-3, 20-dione are added and the solution of kept for 24 hours at 30°. A solution is then added containing 100 ml of water and 5 g of sodium chloride and the resulting mixture is slowly poured into 2,000 ml of acetone under constant agitation. A precipitate is formed which is filtered and washed three times with 100 ml of acetone/water 5:1 and three times with 100 ml of acetone and finally vacuum dried for eight hours at 30°.

4.6 g of the mixed ethanol and desoxycorticosterone ester compound in the title are obtained. Quantitative determination of desoxycorticosterone, after mild alkaline hydrolysis with hydroalcoholic solution of $Na_2CO_3$ and extraction with chloroform, is carried out according to British Pharmacopea, 1980.

Quantitative determination of the ethoxyls is carried out according to R. H. Cundiff and P. C. Markunas [Anal Chem. 33, 1028–1030 (1961)].

EXAMPLE 18

Preparation of the (partial and mixed) ethanol and desoxycorticosterone ester of hyaluronic acid (HY)

40% of carboxylic groups esterified with desoxycorticosterone ($C_{21}$)
40% of salified carboxylic qroups (Na).

6.2 g of HY tetrabutylammonium salt with a molecular weight of 125,000 corresponding to 10 m.Eq. of a monomeric unit are solubilized in 310 ml of dimethylsulfoxide at 25°, 0.62 g (4 m.Eq.) of ethyl iodide are added and the solution is kept for 24 hours at 30°.

0.85 g (2 m.Eq.) of 21-bromo-4-pregnene-3, 20-dione are added and the solution is kept for 24 hours at 30°. A solution is then added containing 100 ml of water and 5 g of sodium chloride and the resulting mixture is slowly poured into 2,000 ml of acetone under constant agitation. A precipitate is formed which is filtered and washed three times with 100 ml of acetone/water 5:1 and three times with 100 ml of acetone and finally vacuum dried for eight hours at 30°.

4.5 g of the partial and mixed ethanol and desoxycorticosterone ester compound in the title are obtained. Quantitative determinations of desoxycorticosterone, after mild alkaline hydrolysis with hydroalcoholic solution of $Na_2CO_3$ and extraction with chloroform, is carried out according to British Pharmacopea, 1980.

Quantitative determination of the ethoxyls is carried out according to R. H. Cundiff and P. C. Markunas Anal. Chem. 33, 1028–1030 (1961)].

EXAMPLE 19

Preparation of the (partial and mixed) ethanol and cortisone ester of hyaluronic acid (HY)

40% of carboxylic groups esterified with ethanol
20% of carboxylic groups esterified with cortisone ($C_{21}$)
40% of salified carboxylic groups (Na).

6.2 g of HY tetrabutylammonium salt with a molecular weight of 125,000 corresponding to 10 m.Eq. of a monomeric unit are solubilized in 310 ml of dimethylsulfoxide at 25°, 0.62 g (4 m.Eq.) of ethyl iodide are added and the solution is kept for 24 hours at 30°.

0.85 g (2 m.Eq.) of 21-bromo-4-pregnen-17 α-ol-3, 11,20-trione are added and the solution is kept for 24 hours at 30°.

A solution is then added containing 100 ml of water and 5 g of sodium chloride and the resulting mixture is slowly poured into 2,000 ml of acetone under constant agitation. A precipitate is formed which is filtered and washed three times with 100 ml of acetone/water 5:1 and three times with 100 ml of acetone and finally vacuum dried for eight hours at 30°.

4.5 g of the partial and mixed ethanol and cortisone compound in the title are obtained. Quantitative determination of cortisone, after mild alkaline hydrolysis with hydroalcoholic solution of $Na_2CO_3$ extraction with chloroform, is carried out according to British Pharmacopea, 1980.

Quantitative determination of the ethoxyls is carried out according to R. H. Cundiff and P. C. Markunas Anal. Chem. 33, 1028–1030 (1961)].

EXAMPLE 20

Preparation of the (partial and mixed) ethanol and hydrocortisone ester ($LC_{21}$) of hyaluronic acid (HY)

40% of carboxylic groups esterified with ethanol
20% of carboxylic groups esterified with hydrocortisone ($C_{21}$)
40% of salified carboxylic groups (Na).

6.2 g of HY tetrabutylammonium salt with a molecular weight of 70,000 corresponding to 10 m.Eq. of a monomeric unit are solubilized in 310 ml of dimethylsulfoxide at 25°, 0.62 g (4 m.Eq.) of ethyl iodide are added and the solution is kept for 24 hours at 30°.

0.85 g (2 m.Eq.) of 21-bromo-4-pregnene-11 β, 17 α-diol-3,20-dione are added and the solution is kept for 24 hours at 30°.

A solution is then added containing 200 ml of water and 5 g of sodium chloride and the resulting mixture is slowly poured into 2,000 ml of acetone under constant agitation. A precipitate is formed which is filtered and washed three times with 100 ml of acetone/water 5:1 and three times with 100 ml of acetone and finally vacuum dried for eight hours at 30°.

4.5 g of the partial and mixed ethanol and hydrocortisone ester compound in the title are obtained. Quantitative determination of hydrocortisone, after mild alkaline hydrolysis with hydroalcoholic solution of $Na_2CO_3$ and extraction with chloroform, is carried out according to British Pharmacopea, 1980.

Quantitative determination of the ethoxyls is carried out according to R. H. Cundiff and P. C. Markunas [Anal. Chem. 33, 1028–1030 (1961)].

EXAMPLE 21

Preparation of the (partial and mixed) ethanol and fluorocortisone esters ($C_{21}$) of hyaluronic acid (HY)

40% of carboxylic groups esterified with ethanol
20% of carboxylic groups esterified with fluorocortisone ($C_{21}$)
40% of salified carboxylic groups (Na).

6.2 g of HY tetrabutylammonium salt with a molecular weight of 65,000 corresponding to 20 m.Eq. of a monomeric unit are solublized in 310 ml of dimethylsulfoxide at 25°, 0.62 g (4 m.Eq.) of ethyl iodide are added and the solution is kept for 24 hours at 30°.

0.89 g (2 m.Eq.) of 9 α-fluoro-21-bromo-4-pregnene-11β, 17 α-diol-3,20-dione are added and the solution is kept for 24 hours at 30°.

A solution is then added containing 100 ml of water and 5 g of sodium chloride and the resulting mixture is slowly poured into 2,000 ml of acetone under constant agitation. A precipitate is formed which is filtered and washed three times with 100 ml of acetone/water 5:1 and three times with 100 ml di acetone and finally vacuum dried for eight hours at 30°.

4.6 g of the partial and mixed ethanol and fluorocortisone ester in the title are obtained. Quantitative determination of fluorocortisone, after mild alkaline hydrolysis with hydroalcoholic solution of $Na_2CO_3$ and extraction with chloroform, is carried out according to British Pharmacopea, 1980.

Quantitative determination of the ethoxyls is carried out according to R. H. Cundiff and P. C. Markunas [Anal. Chem. 33, 1028-1030 (1961)].

EXAMPLE 22

Preparation of the n-pentyl ester of hyaluronic acid (HY)

12.4 g of HY tetrabutylammonium salt with a molecular weight of 620,000 corresponding to 20 m.Eq. of a monomeric unit are solubilized in 620 ml of dimethylsulfoxide at 25°, 3.8 g (25 m.Eq.) of n-pentyl bromide and 0.2 g of iodide tetrabutylammonium are added, the solution is kept for 12 hours at 30°.

The resulting mixture is slowly poured into 3,500 ml of ethyl acetate under constant agitation. A precipitate is formed which is filtered and washed four times with 500 ml of ethyl acetate and finally vacuum dried for twenty four hours at 30°.

8.7 g of the n-pentyl ester product in the title are obtained. Quantitative determination of the ester groups is carried out using the method described on pages 169-172 of Siggia S. and Hann J. G. "Quantitative organic analysis via functional groups" 4th edition John Wiley and Sons.

EXAMPLE 23

Preparation of the isopentyl ester of hyaluronic acid (HY)

12.4 g of HY tetrabutylammonium salt with a molecular weight of 170,000 corresponding to 20 m.Eq. of a monomeric unit are solubilized in 620 ml of dimethysulfoxide at 25°, 3.8 g (25 m.Eq.) of isopentyl bromide and 0.2 g of tetrabutylammonium iodide are added, the solution is kept for 12 hours at 30°.

The resulting mixture is slowly poured into 3,500 ml of ethyl acetate under constant agitation. A precipitate is formed which is filtered and washed four times with 500 ml of ethyl acetate and finally vacuum dried for twenty four hours at 30°.

8.6 g of the isopentyl ester product featured in the title are obtained. Quantitative determination of the ester groups is carried out according to the method described on pages 169-172 of Siggia S. and Hanna J. G. "Quantitative organic analysis via functional groups" 4th edition, John Wiley and Sons.

EXAMPLE 24

Preparation of the benzylester of hyaluronic acid (HY)

12.4 g of HY tetrabutylammonium salt with a molecular weight of 170,000 corresponding to 20 m.Eq. of a monomeric unit are solubilized in 620 ml of dimethylsulfoxide at 25°, 4.5 g (25 m.Eq.) of benzyl bromide and 0.2 g of tetrabutylammonium iodide are added, the solution is kept for 12 hours at 30°.

The resulting mixture is slowly poured into 3,500 ml of ethyl acetate under constant agitation. A precipitate is formed which is filtered and washed four times with 500 ml of ethyl acetate and finally vacuum dried for twenty four hours at 30°.

9 g of the benzyl ester product in the title are obtained. Quantitative determination of the ester groups is carried out according to the method described on pages 169-172 of Siggia S. and Hanna J. G. "Quantitative organic analysis via functional groups" 4th edition, John Wiley and Sons.

EXAMPLE 25

Preparation of the β-phenylethyl ester of hyaluronic acid (HY).

12.4 g of HY tetrabutylammonium salt with a molecular weight of 125,000 corresponding to 20 m.Eq. of a monomeric unit are solubilized in 620 ml of dimethylsulfoxide at 25°, 4.6 g (25 m.Eq.) of 2-bromoethylbenzene and 185 mg of tetrabutylammonium iodide are added, and the solution is kept for 12 hours at 30°.

The resulting mixture is slowly. poured into 3,500 ml of ethyl acetate under constant agitation. A precipitate is thus formed which is then filtered and washed four times with 500 ml of ethyl acetate and finally vacuum dried for twenty four hours at 30°.

9.1 g of the β-phenylethyl ester in the title are obtained. Quantitative determination of the ester groups is carried out according to the method described on page 168-172 of Siggia S. and hanna J. G. "Quantitative organic analysis via functional groups" 4th edition, John Wiley and Sons.

EXAMPLE 26

Preparation of the benzyl ester of hyaluronic acid (HY)

3 g of the potassium salt of HY with a molecular weight of 162,000 are suspended in 200 ml of dimethylsulfoxide; 120 mg of tetrabutylammonium iodide and 2.4 g of benzyl bromide are added.

The suspension is kept in agitation for 48 hours at 30°. The resulting mixture is slowly poured into 1,000 ml of ethyl acetate under constant agitation. A precipitate is formed which is filtered and washed four times with 150 ml of ethyl acetate and finally vacuum dried for twenty four hours at 30°.

3.1 g of the benzyl ester product in the title are obtained. Quantitative determination of the ester groups is carried out according to the method described on pages 169-172 of Siggia S. and Hanna J. G. "Quantitative organic analysis via functional groups" 4th edition, John Wiley and Sons.

EXAMPLE 27

Preparation of streptomycine salt of hyaluronic acid (HY) partially esterified with ethanol 75% of carboxylic groups esterified with ethanol
25% of carboxylic groups salified with streptomycine 243 mg of streptomycine sulphate (1 m.Eq.) are solubilized in 20 ml of water. The solution is eluted in a thermostatic column at 5° containing 2 ml of quaternary ammonium resin (Dowex 1×8) in OH⁻ form.

The sulphate-free eluate is gathered in a thermostatic container at a temperature of 5°.

1.6 g of a 75% ethyl ester of HY and 25% sodium salt (corresponding to 1 m.Eq. of a monomeric unit relative to the non-esterified carboxyl), are solubilized in 400 ml of water. The solution is eluted in a thermostatic column at 20° and containing 2 ml of sulphonic resin (Dowex 50×8) in H⁺ form.

The sodium-free eluate is gathered under agitation in the solution of streptomycine base. The resulting solution is instantly frozen and freeze-dried. Yield: 1.7 g.

Microbiological determination on B.subtilis ATCC 6633 in comparison with streptomycine standard, shows a content of 10.9% in weight of streptomycine base, corresponding to the theoretically calculated content.

EXAMPLE 28

Preparation of the erythromycin salt of hyaluronic acid (HY) partially esterified with ethanol 75% of carboxylic groups esterified with ethanol
25% of carboxylic groups salified with erythromycin 1.6 g of a 75% ethyl ester of HY and sodium salt at 25% (corresponding to m.Eq. of a monomeric unit relative to the non-esterified carboxyl), are solublized in 400 ml of water. The solution is eluted in a thermostatic column at 20° containing 2 ml of sulfonic resin (Dowex 50 ×8) in H⁺ form.

To the sodium-free eluate are added 734 mg of erythromycin base (1 m.Eq.). The resulting solution is instantly frozen and freeze-dried. Yield: 2.1 g.

Microbiological determination on St. aureus ATCC 6538 in comparison to standard erythromycin, shows a content of 31.7% in weight of erythromycin base, corresponding to the theoretically calculated weight.

EXAMPLE 29

Preparation of the neomycin salt of a hyaluronic acid (HY) partially esterified with ethanol 75% of carboxylic groups esterified with ethanol
25% of carboxylic groups salified with neomycin 152 mg of neomycin sulfate (1 m.Eq.) are solubilized in 20 ml of water. The solution is eluted in a thermostatic column at 5° containing 2 ml of quaternary ammonium resin (Dowex 1×8) in OH⁻ form.

The sulphate-free eluate is gathered in a thermostatic container at a temperature of 5°.

1.6 g of a 75% ethyl ester of HY and sodium salt al 25% (corresponding to 1 m.Eq. of monomeric unit relative to the non-esterified carboxyl), are solubilized in 400 ml of water. The solution is eluted in a thermostatic column at 20° and containing 2 ml of sulfonic resin (Dowex 50×8) in H⁺ form.

The sodium-free eluate is gathered under agitation in the solution of neomycin base The resulting solution is instantly frozen and freeze-dried. Yield: 1.65 g.

Microbiological determination carried out on St. aureus ATCC 6538 in comparison to standard neomycin, shows a content of 6.1% in weight of neomycin base, corresponding to the theoretically calculated value.

EXAMPLE 30

Preparation of the gentamicin salt of hyaluronic acid (HY) partially esterified with ethanol 75% of carboxylic groups esterified with ethanol
25% of carboxylic groups salified with gentamicin 145 mg of gentamicin sulfate are solubilized in 10 ml of water. The solution is eluted in a thermostatic column at 5° containing 2 ml of quaternary ammonium resin (Dowec 1×8) in OH⁻ form.

The sulphate-free eluate is gathered in a thermostatic container at a temperature of 5°.

1.6 g of a 75% ethyl ester of HY and sodium salt at 25% (corresponding to 1 m.Eq. of a monomeric unit relative to the non-esterified carboxyl), are solubilized in 400 ml of water. The solution is eluted in a thermostatic column at 20° and containing 2 ml of sulfonic resin (Dowex 50×8) in H⁺ form.

The sodium-free eluate is gathered under agitation in the solution of gentamicin base. The resulting solution is instantly frozen and freeze-dried. Yield: 1.7 g.

Microbiological determination carried out on S. epidermidus ATCC 12228 in comparison to standard gentamicin, shows a content of 6.50% in weight of gentamicin base, corresponding to the theoretically calculated value.

EXAMPLE 31

Preparation of the amikacin salt of hyaluronic acid (HY) partially esterified with ethanol 75% of carboxylic groups esterified with ethanol
25% of carboxylic Groups salified with amikacin 147 mg of amikacin base (1 m.Eq.) are solubilized in 20 ml of water.

147 mg of amikacin (1 m.Eq.) are solubilized in 20 ml of water.

1.6 g of a 75% ethyl ester of HY and sodium salt at 25% (corresponding to 1 m.Eq. of a monomeric unit relative to the non-esterified carboxyl), are solubilized in 400 ml of wter. The solution is eluted in a thermostatic column at 20° and containing 2 ml of sulfonic resin (Dowex 50×8) in H⁺ form.

The sodium-free eluate is gathered under agitation in the solution of amikacin base. The resulting solution is instantly frozen and freeze-dried. Yield: 1.70 g.

Microbiological determination carried out on St. aureus ATCC 29737 in comparison to standard amikacin, shows a content of 8.5% in weight of amikacin base, corresponding to the theoretically calculated value.

EXAMPLE 32

Preparation of the kanamycin salt of hyaluronic acid (HY) partially estified with ethanol 75% of carboxylic qroups esterified with ethanol 25% of carboxylic qroups salified with kanamycin 146 mg of kanamycin sulfate (1 m.Eq.) are solubilized in 20 ml of water. The solution is eluted in a thermostatic column at 5° containing 2 ml of quaternary ammonium resin (Dowex 1×8) in OH⁻ form.

The sulphate-free eluate is gathered in a thermostatic container at a temperature of 5°.

1.6 g of a 75% ethyl ester of HY and sodium salt at 25% (corresponding to 1 m.Eq. of a monomeric unit relative to the non-esterified carboxyl), are solubilized in 400 ml of water. The solution is eluted in a thermostatic column at 20° and containing 2 ml of sulfonic resin (Dowex 50×8) in H+ form.

The sodium-free eluate is gathered under agitation in the solution of kanamycin base. The resulting solution is instantly frozen and freeze-dried. Yield: 1.5 g.

Microbiological determination carried out on B. subtilis ATCC 6633 in comparison to standard kanamycin, shows a content of 7% in weight of kanamycin base, corresponding to the theoretically calculated value.

EXAMPLE 33

Preparation of the pilocarpine salt of hyaluronic acid (HY) partially esterified with ethanol 75% of carboxylic groups esterified with ethanol
25% of carboxylic groups salified with pilocarpine 245 mg of pilocarpine hydrochloride (1 m.Eq.) are solubilized in 20 ml of water. The solution is eluted in a thermostatic column at 5° containing 2 ml of quaternary ammonium resin (Dowex 1×8) in OH⁻ form.

The chloride-free eluate is gathered in a thermostatic container at 5°.

1.6 g of a 75% ethyl ester of HY and sodium salt at 25% (corresponding to 1 m.Eq. of a monomeric unit relative to the non-esterified carboxyl), are solubilized in 400 ml of water. The solution is eluted in a thermostatic column at 20° and containing 2 ml of sulfonic resin (Dowex 50×8) in H+ form.

The sodium-free eluate is gathered under agitation in the solution of pilocarpine base. The resulting solution is instantly frozen and freeze-dried. Yield: 1/89 g.

EXAMPLE 34

Preparation of the (partial propyl) ester of hyaluronic acid (HY)

85% of esterified carboxylic groups
15% of salified carboxylic groups (Na)

12.4 g of HY tetrabutylammonium salt with a molecular weight of 165,000 corresponding to 20 m.Eq. of a monomeric unit are solubilized in 620 ml of dimethysulfoxide at 25°, 2.9 g (17 m.Eq.) of propyl iodide are added and the resulting solution is kept for 12 hours at 30°.

A solution is then added containing 62 ml of water and 9 g of sodium chloride and the resulting mixture is slowluy poured into 3,500 ml of acetone under constant agitation. A precipitate is formed which is filtered and washed three times with 500 ml of acetone/water 5:1 and three times with acetone and finally vacuum dried for eight hours at 30°.

The product is then dissolved in 550 ml of water containing 1% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30°. 8 g of the partial propyl ester compound in the title are obtained. Quantitative determination of the ester groups is carried out using the method of R. H. Cundiff and P. C. Markunas [Anal. Chem. 33, 1028–1030, (1961)].

EXAMPLE 35

Preparation of the pilocarpine salt of hyaluronic acid (HY) partially esterified with n-propanol 85% of carboxylic groups esterified with n-propanol
15% of carboxylic groups salified with pilocarpine 245 mg of pilocarpine hydrochloride (1 m.Eq.) are solubilized in 10 ml of water. The solution is eluted in a thermostatic column at 5° containing 2 ml of quaternary ammonium resin (Dowex 1×8) in OH⁻ form.

The chloride-free eluate is gathered in a thermostatic container at 5°.

4.1 g. o f the p ropyl ester of HY 85 % and tetrabutylammonium salt at 15% (corresponding to 1 m.Eq. of a monomeric unit relative to the non-esterified carboxyl) are solubilized in 100 ml of dimethylsulfoxide. The solution is eluted in a thermostatic column at 20° containing 2 ml of damp sulfonic resin (Dowex 50×8) in H+ form.

The eluate is gathered under agitation in the solution of pilocarpine base. The resulting solution is precipitated with ethyl acetate (600 ml).

The precipitate is filtered and washed four times with 200 ml of ethyl acetate and finally vacuum dried for 24 hours at 30°. 3.5 g of the compound featured in the title are obtained.

EXAMPLE 36

Preparation of the ethyl ester of an acidic polysaccharide producted by Rhinocladiella eliator The acidic polysaccharide produced by Rhinocladiella eliator Mangenot NRRL YB-4613 is used (P. R. Watson, P. A. Sandford, K. A. Burton, M. C. Cadmus and A. Jeanes - Carbohydr. Res. 46, 259–265 (1976); L. Kenne, B. Lindberg, K. Peterson and P. Unger, Carbohydr. Res. 84, 184–186 (1980). It is made up of units of 2-acetamido-2-deoxy-D-glucuronic acid connected by bonds 1→4.

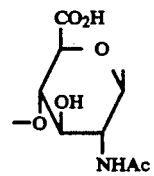

5.2 g of the potassium salt of this acidic polysaccharide, corresponding to 20 mEq of a monomeric unit, are suspended in 250 ml of dimethylsulfoxide. While the mixture is kept in agitation, 200 mg of tetrabutylammonium iodide are added at 3° C. and then slowly 3.5 g of methyl iodide. The mixture is kept in agitation for 48 hours at 35° C., after which it is slowly poured into 800 ml of ethyl acetate, keeping it under constant agitation. A precipitate is formed which is filtered and washed four times with 150 ml of ethyl acetate and lastly vacuum dried. 4 g of the ethyl ester product in the title are thus obtained, in which all the carboxylic groups are esterified. Quantitative determination of the ester groups is carried out by the method of R. H. Cundiff and P. C. Markanas Anal. Chem. 33, 1028–1030 (1961).

EXAMPLE 37

Preparation of the ethyl ester of acid polysaccharide produced by Rhinocladiella eliator 10.0 g of the tetrabutylammonium salt of the acidic polysaccharide used as starting substance in Example 36, corresponding to 20 mEq of a monomeric unit, are treated with 800 ml of dimethylsulfoxide at 30° C. 3.3 g (21.2 mEq) of ethyl iodide are added and the solution is kept under agitation for 48 hours at 30° C. The resulting mixture is slowly poured into 4000 ml of ethyl acetate while kept under constant agitation. A precipitate is formed which is filtered and washed four times with 500 ml of ethyl acetate and lastly vacuum dried.

3 g of the ethyl ester product in the title are obtain, in which all the carboxylic groups are esterified.

Quantitative determination of the ester groups is carried out by the method of R. H. Cundiff and P. C. Markanas [Anal. Chem. 33, 1028–1030, (1961)].

EXAMPLE 38

Preparation of the ethyl ester of the acidic polysaccharide produced by Rhinocladiella Mansoni Acidic polysaccharide produced by Rhinocladiella Mansoni NRRL Y-46272 [(A. Jeanes, K. A. Burton, M. C. Cadmus, C. A. Knutson, G. L. Rowin and P. A. Sandford—Nature (London) 233, 259–260 (1971); P. A. Sandford, P. A. Watson and A. P. Jeanes—Carbohydr. Res. 29, 153–166 (1973)]. It is made up of units formed by one molecule of 2-acetamido-2-deoxy-D-glucuronic acid and two molecules of N-acetyl-D-glucasamine connected by bonds 1→3.

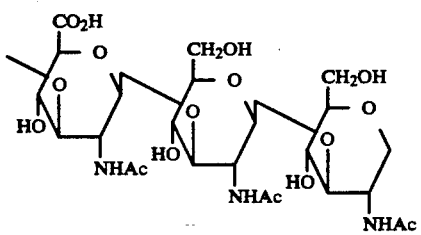

18.2 g of tetrabutylammonium salt of this acidic polysaccharide, corresponding to 20 mEq of a monomeric unit, are treated with 1000 ml of dimethylsulfoxide at 30° C. Under agitation, 3.3 g (21.2 mEq) of ethyl iodide and the solution is kept at 30° C. for 24 hours, after which it is slowly poured into 4000 ml of ethyl acetate, keep it under constant agitation. A precipitate is formed which is filtered and washed four times with 500 ml of ethyl acetate and lastly vacuum dried.

11 g of the product featured in the title are obtained, in which all the carboxylic groups are esterified. Quantitative determination of the ester groups is carried out according to the method of R. H. Cundiff and P. C. Markanas [Anal. Chem. 33, 1028–1030, (1961)].

BIOLOGICAL ACTIVITY STUDIES

1) Anti-inflammatory Activity Studies

The technical effect of the new esters and of the new medicaments according to the invention may be demonstrated for example by placing in evidence the antiinflammatory activity of some partial esters of hyaluronic acid with antiphlogistic corticosteroids, measured in the model of exudative phlogosis induced by dextran in rabbit eye.

Materials 9 hyaluronic esters of cortisone, hydrocortisone and fluorocortisone (9 - fluorohydrocortisone) identified by the code names HYC1–HYC9 were tested. Table 1 describes these compounds and gives the percentages of the number of carboxylic groups of HY which are esterified with the above corticosteroids, and where applicable the percentage esterified with simple aliphatic alcohols and those salified with alkaline metals (Na):

The activity of the compounds of Table 1 was compared with the corresponding cortisones.

TABLE 1

| COMPOUND | % CARBOXYLS ESTERIF. WITH CORTICOSTEROIDS | CORTI-COSTEROID ASSAY (p/p) | % CARBOXYLS ESTERIF. WITH ALIPHATIC ALCOHOL | ALIFATIC ALCOHOL ASSAY (p/p) | % CARBOXYLS SALIFIED WITH Na |
|---|---|---|---|---|---|
| HYC1 | 20 CORTISONE | 15.5% | — | — | 80 |
| HYC2 | 20 HYDROCORTISONE | 15.6% | — | — | 80 |
| HYC3 | 20 FLUDROCORTISONE | 16.2% | — | — | 80 |
| HYC4 | 20 CORTISONE | 15.3% | 80 ETHANOL | 7.84% | / |
| HYC5 | 20 HYDROCORTISONE | 15.4% | 80 ETHANOL | 7.83% | / |
| HYC6 | 20 FLUDROCORTISONE | 16.1% | 80 ETHANOL | 7.77% | / |
| HYC7 | 20 CORTISONE | 15.4% | 40 ETHANOL | 3.94% | 40 |
| HYC8 | 20 HYDROCORTISONE | 15.5% | 40 ETHANOL | 3.94% | 40 |
| HYC9 | 20 FLUDROCORTISONE | 16.1% | 40 ETHANOL | 3.91% | 40 |

All the derivatives, except for HYC4, HYC5 and HYC6 (dissolved in DMSO) were dissolved in saline (2 mg/ml).

Method

Aseptic (exudative) phlogosis was induced in 48 rabbits by intraocular injection of dextran (1% in saline, 0.1 ml). The various products were administered by instillation in the right eye (RE) of the rabbits, while in the left eye (LE) only vehicle was instilled.

The treatment (3 drops every 6 hours) was begun immediately after the injection of dextran and was continued for 16 days.

Ophthalmic Examination

Both eyes of each rabbit were observed through a slit lamp. In particular the following were examined: the state of the conjunctiva and corneal epithelium, the anterior chamber (presence of Tyndall effect), state of the iris and of the posterior segment of the eye. With a Goldmann lens, the state of the back of the eye was examined. The presence of signs of inflammation (hyperemia, exudate, cloudiness of the liquids, etc.) was recorded. The percentage of the eyes which did not present any signs of phlogisis was then calculated. Results As can be observed from the results reported in Table 2, the HYC derivatives all proved to possess a considerable antiinflammatory activity consistently superior to that of the corresponding cortisones tested in parallel, reduced not only the percentage of eyes with phlogosis on each day of observation, but also reducing the duration of inflammation. The most efficient of these derivatives seem to be HYC4, HYC5 and HYC6, presumably because they are more lipophilic.

TABLE 2

Antiinflammatory effect of the HYC derivatives (hyaluronic esters) on dextran-induced aseptic (exudative) phlogosis in rabbit eye

| Treatment | Days from start of phlogosis | | | | | | | |
|---|---|---|---|---|---|---|---|---|
| | 2 | 4 | 6 | 8 | 10 | 12 | 14 | 16 |
| Cortisone (4) | 0.0 | 0.0 | 0.0 | 0.0 | 25.0 | 50.0 | 100.0 | 100.0 |
| Vehicle (4) | 0.0 | 0.0 | 0.0 | 0.0 | 0.0 | 25.0 | 25.0 | 50.0 |
| Hydrocortisone (4) | 0.0 | 0.0 | 0.0 | 25.0 | 25.0 | 50.0 | 100.0 | 100.0 |
| Vehicle (4) | 0.0 | 0.0 | 0.0 | 0.0 | 0.0 | 25.0 | 50.0 | 100.0 |
| Fluorocortis. (4) | 0.0 | 0.0 | 0.0 | 0.0 | 25.0 | 50.0 | 100.0 | 100.0 |
| Vehicle (4) | 0.0 | 0.0 | 0.0 | 0.0 | 0.0 | 50.0 | 50.0 | 100.0 |
| HYC1 (4) | 0.0 | 0.0 | 0.0 | 25.0 | 50.0 | 50.0 | 100.0 | 100.0 |
| Vehicle (4) | 0.0 | 0.0 | 0.0 | 0.0 | 00.0 | 25.0 | 50.0 | 100.0 |
| HYC2 (4) | 0.0 | 0.0 | 0.0 | 25.0 | 50.0 | 100.0 | 100.0 | 100.0 |
| Vehicle (4) | 0.0 | 0.0 | 0.0 | 0.0 | 00.0 | 25.0 | 50.0 | 100.0 |
| HYC3 | 0.0 | 0.0 | 0.0 | 25.0 | 25.0 | 100.0 | 100.0 | 100.0 |
| Vehicle (4) | 0.0 | 0.0 | 0.0 | 0.0 | 00.0 | 25.0 | 50.0 | 100.0 |
| HYC4 (4) | 0.0 | 0.0 | 25.0 | 50.0 | 50.0 | 100.0 | 100.0 | 100.0 |
| Vehicle (4) | 0.0 | 0.0 | 0.0 | 0.0 | 00.0 | 25.0 | 50.0 | 100.0 |
| HYC5 (4) | 0.0 | 0.0 | 25.0 | 50.0 | 50.0 | 100.0 | 100.0 | 100.0 |
| Vehicle (4) | 0.0 | 0.0 | 0.0 | 0.0 | 00.0 | 25.0 | 50.0 | 100.0 |
| HYC6 (4) | 0.0 | 0.0 | 25.0 | 50.0 | 50.0 | 100.0 | 100.0 | 100.0 |
| Vehicle (4) | 0.0 | 0.0 | 0.0 | 0.0 | 00.0 | 25.0 | 25.0 | 50.0 |
| HYC7 (4) | 0.0 | 0.0 | 0.0 | 25.0 | 50.0 | 100.0 | 100.0 | 100.0 |
| Vehicle (4) | 0.0 | 0.0 | 0.0 | 0.0 | 00.0 | 25.0 | 50.0 | 50.0 |
| HYC8 (4) | 0.0 | 0.0 | 0.0 | 25.0 | 50.0 | 100.0 | 100.0 | 100.0 |
| Vehicle (4) | 0.0 | 0.0 | 0.0 | 0.0 | 00.0 | 50.0 | 50.0 | 50.0 |
| HYC9 (4) | 0.0 | 0.0 | 0.0 | 25.0 | 25.0 | 50.0 | 100.0 | 100.0 |
| Vehicle (4) | 0.0 | 0.0 | 0.0 | 0.0 | 00.0 | 50.0 | 50.0 | 100.0 |

Values are expressed as percentages (number of eyes without signs of phlogosis out of the total number of eyes treated). In brackets are the number of treated eyes.

2) Absorption and Bioavailability Studies

The technical effect of the new products according to the present invention may be demonstrated by a study of the absorption and of the bioavailability of some derivatives of hydrocortisone with hyaluronic acid. The derivatives used are those described above and identified as HYC2, HYC5 and HYC8.

Materials and Methods

Animals

Male Sprague-Dawley rats, with a body weight of 250–350 gr were used, obtained from Charles River-Calco (Como), fed ad libitum with water and compound feed in pellets, with the code name of 4RF 21, produced by "Italiana Mangimi", licensee of Charles River.

Treatment

Hydrocortisone was administered in the form of sodium hemisuccinate salt at the dose of 1.34 mg/kg (corresponding to 1 mg/kg of hydrocortisone base) by general intravenous route and at the dose of 1.34 mg/kg and 2.68 mg/kg (corresponding to 2 mg/kg of hydrocortisone base) by subcutaneouos route (the i.v. route was considered in order to determine the pharmacokinetic parameters which serve as a comparison for the evaluation of absorption of any other administration route).

The three HYC derivatives were administered by subcutaneous route at the dose of 6.5 and 13 mg/kg (doses corresponding to about 1 and 2 mg/kg in hydrocortisone base). All the various products were dissolved in sterile saline, except for HYC5 which, being insoluble in completely aqueous solutions, was first solubilized with the addition of the minimum quantity necessary of dimethyulsulphoxide, and then brought to the right volume with saline. All the compounds were injected at a constant volume of 1 ml/kg.

Gathering of the Plasma Samples

After administration, 0.3 ml of blood was drawn from each animal by cardiac puncture in the presence of anticoagulant (sodium heparin).

Blood drawing times were as follows: *15 mins, 30 mins, 60 mins, 120 mins, 180 min, 300 mins, 360 mins, 420 mins, 480 mins (*limited to the intraveneous route).

Dosage of Hydrocortisone

The hydrocortisone was dosed by radioimmunoassay method (Cortisolo Kit, Biodata, cod. 10394) using iodate tracing. The precision and accuracy of the method, determined on six repeats (double) of a control serum with a known control assay, proved to be 3.03% and 0.021% respectively. The linearity of the method comes between 1 and 1000 ng/ml. The observation limit is 1 ng/ml.

The dosage of the cortisolemia in the rat is not influenced either by the base levels or by the circadian rhythms of this hormone, as the metabolic pattern of the endogenous glucocorticoid hormones in the rat, leads to the production of corticosterone and not cortisol (see E. L. Green: Biology of the laboratory mouse.)

Preliminary proof has demonstrated that the dosage method is specific only for free cortisol. The anticortisol antibody does not present any form of competition towards any of the three HYC derivatives.

Results

In Table 3 are reported the results of the average plasma levels of hydrocortisone, after i.v. and s.c. injection (1 and 2 mg/kg). It should be emphasized that, after s.c. injection, there is a quite rapid absorption of the product (Tmax evaluated at about 30 mins, Cmax the same as the i.v. route levels at the same dose). In Table 4 are reported the pharmacokinetic parameters of cortisol calculated graphically from the plasmatic decline curves. In Table 3 are reported the average levels of cortisol after subcutaneous administration of the three HYC derivatives at doses of 6.5 and 13 mg/kg (corresponding to about 1 and 2 mg/kg in hydrocortisone base). In Table 4 are reported the pharmacokinetic parameters relative to cortisol calculated graphically with the method of residues from the plasma absorption curve of the three HYC products.

It should be noted that the kinetics of hydrocortisone released by the three derivatives with hyaluronic acid are not linear; that is, no direct relationship exists between the dose-dependent parameters such as the area beneath the plasma decline curve and the plasma levels. Since the kinetics of cortisol are themselves linear and a first rate model results, it can be deduced that the saturation process in the case of the HYC derivatives is the hydrolisis of the ester bond between hyaluronic acid and cortisolo. This phase (tending towards zero rate kinetics) is not itself connected with the absorption of the active principle and therefore the kinetics of the three HYC's were likewise resolved according to a first rate model.

great deal according to its storage capacity (values vary between 10% and 60% of water content). The skin's humidity depends on a series of endogenous and exogenous factors.

Cutaneous humidity fundamentally influences the formation of the skin's specific hydrolipidic film which modifies and stores the substances it eliminates, thus forming the basis for the realization of its protective

TABLE 3

Average plasmatic levels of hydrocortisone after s.c. administration of the derivatives $HYC_2$—$HYC_5$—$HYC_8$ (6.5 and 13 mg/kg) in comparison to the corresponding doses (1-2 mg/Kg) of hydrocortisone (average of 4 values)

AVERAGE PLASMATIC LEVELS (mg/ml)

| TIME minutes | s.c. HYDROCORTISONE i.v. 1 mg/kg | 1 mg/kg | 2 mg/kg | s.c. $HYC_2$ 6.5 mg/kg | 13 mg/kg | s.c. $HYC_5$ 6.5 mg/kg | 13 mg/kg | s.c. $HYC_8$ 6.5 mg/kg | 13 mg/kg |
|---|---|---|---|---|---|---|---|---|---|
| 15 min | 154.57 | | | | | | | | |
| 30 min | 88.50 | 86.29 | 196.32 | 27.02 | 32.32 | 33.41 | 26.55 | 33.75 | 34.62 |
| 60 min | 59.62 | 61.27 | 142.12 | 35.67 | 50.51 | 49.52 | 38.77 | 45.23 | 51.69 |
| 120 min | 46.97 | 49.10 | 84.34 | 42.32 | 62.42 | 60.52 | 41.56 | 44.75 | 108.01 |
| 180 min | 39.35 | 23.44 | 50.02 | 37.35 | 58.44 | 61.17 | 44.81 | 41.80 | 76.64 |
| 300 min | 29.78 | 11.98 | 24.53 | 32.27 | 51.68 | — | 32.51 | 30.00 | 54.66 |
| 360 min | 24.49 | 9.96 | 20.15 | 26.96 | 48.17 | 42.44 | 31.92 | 26.10 | 47.17 |
| 420 min | 21.88 | 8.48 | 16.81 | 24.24 | 44.67 | 30.43 | 26.17 | 20.50 | 42.60 |
| 480 min | 18.31 | 7.61 | 14.81 | 18.92 | 39.41 | 25.85 | 22.54 | 17.60 | 37.03 |

TABLE 4

Pharmacokinetic parameters of hydrocortisone after subcutaneous administration of $HYC_2$, $HYC_5$, $HYC_8$ at a dose of 6.5 mg/kg in comparison to the corresponding dose of hydrocortisone (1 mg/kg)

| PARAMETERS | HYDROCORTISONE | $HYC_2$ | $HYC_5$ | $HYC_8$ |
|---|---|---|---|---|
| $K_e$ | $0.15\ h^{-1}$ | $0.17\ h^{-1}$ | $0.24\ h^{-1}$ | $0.19\ h^{-1}$ |
| t ½ elim. | 4.5 h | 4.08 h | 2.89 h | 3.65 h |
| $k_a$ | | $0.86\ h^{-1}$ | $0.65\ h^{-1}$ | $0.94\ h^{-1}$ |
| $t_{max}$ | 30 min. | 2.35 h | 2.4 h | 2.13 h |
| $(AUC)_8^{0.5}$ | 192.00 ng/ml h | 241.06 ng/ml h | 278.92 ng/ml h | 250 ng/ml h |
| Bioavailability | 70.3 | 88.3% | 100% | 91% |

Conclusions

The bioavailability, as compared to hydrocortisone, of the three products in examination, proves to be complete and even superior to that of the quick release preparation. Regarding this, however, the absorption is slower (maximum time about 2 hrs) and maximum concentrations equal to those of subcutaneously administered cortisol are not reached. The plasmatic cortisolemia proves however on average to be higher several hours after administration. Esterification with hyaluronic acid therefore determines slower release of hydrocortisone, and this is the desired objective.

3) Skin Hydration Studies

Hydrolysis of the ester bond, as has already been said, is a saturation process; that is, it tends towards zero grade kinetics. This, for a retard form, is a very desirable factor, since, by definition, a controlled release preparation is "a preparation which determines the release of a constant aliquot of active principle in a given time" and this is the condition reached by zero grade kinetics.

The skin, due to the complex nature of its physiological functions, cannot be considered as exclusively a passive covering organ, but rather as a dynamic, polyvalent organ. The complete functional capacity of the skin is fundamentally guaranteed by the presence of an intact hydrolipidic covering and this requires a correct humidity content in the horny layer, which varies a functions.

The means of defense used so far to restore the maximum degree of hydration for the skin involve the use of highly hygroscopic substances, such as glycerine, sodium lactate and propylenic glycol. These substances, however, had the disadvantage, in dry conditions, of drawing humidity from the skin itself instead of from the external environment, thus making the skin even drier.

For this reason at present there is a preference for biological substances whose origins lie, for their particular characteristics, to the natural hydrating factors mentioned before. In this context is included the considerable interest in the use of hyaluronic acid.

The hydration of the skin and its nourishment seem closely related to the HY content of the cutaneous tissue. It has in fact been demonstrated that the exogeneous contribution of HY contributes noticeably to the state of hydration of the cutaneous tissue.

These particular characteristics of hyaluronic acid are also found, and to an even greater degree, in the esterified derivatives of HY according to the present invention, and for this reason they may be used to a great extent in the field of cosmetics.

In order to establish a comparison between hyaluronic acid and its derivatives of the present invention, some experiments were carried out to instrumentally evaluate, after topical application, the hydrating properties of the compounds in examination.

Materials

As hyaluronic derivatives according to the present invention the following esters were used.

HYAFF$_2$ hyaluronic acid esterified by 75% with methanol

HYAFF$_7$ hyaluronic acid esterified by 75% with ethanol

HYAFF$_8$ hyaluronic acid esterified by 50% with isopropanol

HYAFF$_9$ hyaluronic acid esterified by 50% with n-propanol

HYAFF$_{10}$ hyaluronic acid esterified by 50% with n-butanol

Hyaluronic acid sodium salt (Hyalastine fraction)

All the compounds were vehicled at a concentration of 0.2% in an ointment the composition of which was as follows:

Polyethylenglycol monostearate 400, gr. 10.000
Cetiol V, gr. 5.000
Lanette SX, gr. 2.000
Paraoxybenzoate of methyl, gr. 0.075
Paraoxybenzoate of propyl, gr. 0.050
Sodium dehydroacetate, gr. 0.100
Glycerine F.U., gr. 1.000
Sorbitol 70, gr. 1.500
Test cream, gr. 0.050
Water for injectable prepar. q.b.a., gr. 100.000

The placebo formulation contained only vehicle.

Method

Study Sample

The study was carried out on 10 healthy volunteers (6 women and 4 men not suffering from any form of skin disease), aged between 20 and 60 years.

Treatment

Each volunteer was treated (single administration) with all the formulations in examination, which were applied (1 gr./ointment) to the inside surface of each forearm, distinguishing with a dermographic pencil the application zone (about 25 cm$^2$) of each product and standardizing the procedure as far as possible. To the right forearm were applied the compounds known as HYAFF$_2$, HYAFF$_7$, HYAFF$_8$, HYAFF$_9$, while to the left were applied HYAFF$_{10}$, placebo and hyaluronic acid.

Evaluation Parameters

At the established times (0, 3, 6 and 24 hours after treatment) the degree of hydration was measured with a corneometer of the horny layer of each application zone.

Most particularly, the dielectric strength of the water was measured (in 0.8 seconds), after application of the sensor (condenser) to the skin surface. The value thus obtained, the measurement unit of which corresponds to 0.07 mg of water (normal values are between 90 and 100 units), was read on the dial of the instrument.

Registrations were carried out in constant humidity conditions.

Results

As can be seen from the results reported in Table 5, treatment with the compounds of the HYAFF series induced, in all cases, a notable increase in the degree of hydration of the horny layer, which was particularly evident not only during the hours immediately following application, but also from the last registrations. This effect proved to be superior both to that of the placebo formulation and to the formulation containing hyaluronic acid sodium salt. Of the compounds tested, the derivatives HYAFF$_2$ and HYAFF$_9$ appeared particularly interesting.

Conclusions

On the basis of the results obtained it was possible to conclude that the esterified HYAFF derivatives do in fact determine a notable and prolonged hydrating effect at the skin level, which is superior to that observed with the formulation containing hyaluronic acid, thus guaranteeing the integrity and physiological efficiency of the hydrolipidic film. These satisfactory results form therefore a valid basis for the use of these compounds in the prevention (or treatment) of chapped skin, the treatment of burns and scalds and the maintaining of physiological nourishment and elasticity of the skin.

TABLE 5

Effect of the compounds of the HYAFF series on the degree of hydration of the corneal layer (each value represents the average for 10 subjects)

| PRODUCT | x Δ% 1st hr | x Δ% 3rd hr | x Δ% 6th hr | x Δ% 24th hr |
|---|---|---|---|---|
| PLACEBO | 41.5 | 28.3 | 13.4 | 2.2 |
| HYALURONIC ACID | 54.7 | 37.6 | 19.7 | 5.3 |
| HYAFF$_2$ | 66.6 | 43.1 | 24.5 | 6.1 |
| HYAFF$_7$ | 93.5 | 66.7 | 30.1 | 11.4 |
| HYAFF$_8$ | 70.0 | 51.4 | 26.2 | 8.7 |
| HYAFF$_9$ | 81.0 | 59.9 | 29.0 | 9.6 |
| HYAFF$_{10}$ | 68.8 | 57.0 | 27.5 | 8.3 |

4) Enzyme Stability and Oxygen Permeability Studies.

Materials

The valuable properties of the new esters according to the present invention, already partially described, which form their technical advantages over the already known products in the respective fields are further illustrated by the following results on the stability of the enzymes and the permeability to oxygen of the films obtained with the following compounds:

HYAFF$_2$ hyaluronic acid esterified by 100% with methanol

HYAFF$_7$ hyaluronio acid esterified by 100% with ethanol

HYAFF$_8$ hyaluronic acid esterified by 100% with isopropanol

HYAFF$_9$ hyaluronic acid esterified by 100% with n-propanol

HYAFF$_{11}$ hyaluronic acid esterified by 100% with benzylic alcohol

HYAFF$_{20}$ hyaluronic acid esterified by 100% with β-phenylethylic alcohol

HYAFF$_{22}$ hyaluronic acid esterified by 100% with isopentylic alcohol

The films may be prepared according to the method described in Example 39.

Stability to Enzymes of the HYAFF Films

Stability to Serum Esterage

Each film (weighing about 20 mg.) was placed in a polyethylene capsule together with 5 ml of rabbit serum and kept at a constant temperature (37° C.).

The evaluation parameter was the time taken (in hours) for the film to dissolve. The results are reported in Table 6.

Stability to hyaluronidase

Each film (weighing about 20 mg.) was placed in a polyethylene capsule together with pH 5 buffer (acetate 0.1M, NaCl 0.15M) or pH 7.2 (phosphate 0.1M, NaCl 0.15M) containing 100 U of enzyme (testicle hyaluronidase from Miles batch 8062, activity 342 turbidometric units/mg) in each ml and kept at a constant temperature (37° C.). The evaluation parameter was the time taken (in hours) for the film to dissolve. The results are reported in Table 6.

TABLE 6

Stability of the films of the HYAFF series derivatives in the presence of serum esterase (37° C.) and in the presence of hyaluronidase (37° C.; pH 5 and pH 7.2)

| COMPOUNDS | STABILITY (hrs) SERUM ESTERASE | HYALURONIDASE pH 5 | HYALURONIDASE pH 7.2 |
|---|---|---|---|
| HYAFF$_2$ | 72 | 120 | 120 |
| HYAFF$_9$ | 120 | 168 | 168 |
| HYAFF$_7$ | 90 | 150 | 150 |
| HYAFF$_{11}$ | 60 | 140 | 140 |
| HYAFF$_{20}$ | 130 | 180 | 180 |
| HYAFF$_{22}$ | 130 | 175 | 175 |

Permeability to oxgycen of the films of the HYAFF series

Each film was placed in a container having 2 compartments separated by the membrane itself. One compartment (volume=1, 2 cc) was filled with partially degassed water (PO$_2$=45 mm of Hg at 23° C.), into the other was introduced a flow of O$_2$ and CO$_2$ (95% and 5% respectively), kept constant (1 bubble/second) in time. The whole system was insulated in nitrogen.

At the established times (15, 30, 60, 90, 120, 240 minutes) a suitable aliquot of water was drawn off (1.2 cc) and determination of the partial pressure of O$_2$ was effected by a Gas System analyser 1302 from the Instrumentation Laboratories. The saturation pressure (550 mg of Hg) was taken as reference value and calculated, in the previously described experimental conditions, by insufflating the O$_2$ atmosphere.

The tests were carried out in comparison to an impermeable membrane and silastic (Lepetit cat. No. 500-1). The results are reported in Table 7.

TABLE 7

PERMEABILITY TO O$_2$ OF THE FILMS OF THE HYAFF SERIES

| COMPOUNDS | PRESSURE OF O$_2$ (mm Hg at 23° C.) | | | | | | |
|---|---|---|---|---|---|---|---|
| | 0 min | 15 min | 30 min | 60 min | 90 min | 120 min | 240 min |
| non perm. membrane | 45 | 90 | 90 | 90 | 90 | 90 | 90 |
| Silastic | 45 | 340 | 406 | 422 | 422 | 422 | 430 |
| HYAFF$_2$ | 45 | 226 | 285 | 300 | 348 | 390 | 390 |
| HYAFF$_9$ | 45 | 250 | 303 | 320 | 371 | 427 | 420 |
| HYAFF$_7$ | 45 | 241 | 298 | 315 | 330 | 340 | 386 |
| HYAFF$_{11}$ | 45 | 260 | 310 | 328 | 350 | 400 | 400 |
| HYAFF$_{20}$ | 45 | 215 | 256 | 317 | 337 | 380 | 375 |
| HYAFF$_{22}$ | 45 | 249 | 288 | 310 | 352 | 373 | 370 |

PHARMACEUTICAL PREPARATIONS

One object of the present invention is the provision of pharmaceutical preparations containing one or more of the above mentioned esters of hyaluronic acid and salts thereof, or one or more medicaments resulting from the association of one of such esters with a pharmacologically active substance for topical application, as described above. That is medicaments in which the hyaluronic ester acts as a vehicle for the active substance.

The pharmaceutical preparations containing the hyaluronic esters as an active principle, both in the case of esters with therapeutically inactive alcohols destined for the same uses as hyaluronic acid itself, and esters with therapeutically active alcohols intended for the usual uses of such alcohols, contain the usual excipients and may be employed for oral, rectal, parenteral, subcutaneous, local or intradermal use. They are therefore in solid or semisolid form, for example as pastilles, tablets, gelatin capsules, capsules, suppositories, soft gelatin capsules. For parenteral and subcutaneous use it is possible to use forms intended for intramuscular or intradermal administration, or suitable for infusions or intravenous injections. It is possible therefore to provide solutions of the active compounds or freeze dried powders of the active compounds to be added to one or more pharmaceutically acceptable excipients or diluents, convenient for the above mentioned uses and with osmolarity compatible with the physiological liquids. For local use, preparations in spray form may be used, for example nasal sprays, creams or ointments for topical use or specially prepared sticking plasters for intradermal administration. The solubility of the hyaluronic esters in organic solvents with low boiling points makes them particularly suitable for the manufacture of "sprays".

The preparations of the invention may be administered to man or animals. They contain preferably between 0.01% and 10% of active component for the solutions, sprays, ointments and creams and between 1% and 100%, preferably between 5% and 50%, of active compound for the preparations in solid form. The dosage to be administered will depend on individual needs, on the desired effect and on the chosen administration route. The daily dosage of such preparations may be decided according to that use for the corresponding known preparations both of hyaluronic acid for the corresponding cures, for example for the cure of arthritis, for example in man or horse, and of the therapeutically active alcohol, the action of which is to be put to use. Thus, for example, the dosage of a hyaluronic ester with cortisone may be derived from its content of this steroid and from its usual dosage in the known pharmaceutical preparations.

One particular form of pharmaceutical preparations is represented by the above mentioned medicaments containing the association of an hyaluronic ester and of one or more active substances. These may also be in solid form, for example as freeze dried powders containing only the two components (1) and (12), together or separate. This galenic form is especially suitable for topical use. Indeed these solid medicaments form, on contact with the surfaces to be treated, more of less concentrated solutions according to the nature of the particular epithelium, with the same characteristics of the solutions previously prepared in vitro and which represent another particularly important aspect of the present invention. Such solutions are preferably in distilled water or sterile saline and preferably contain no other pharmaceutical vehicle apart from the hyaluronic ester or one of its salts. The concentrations of such solutions may also vary within ample limits, for example between 0.01 and 75% both for each of the two components taken separately, and for their mixtures or salts. Particular preference is given to solutions with a pronounced elastic-viscous character, for example with a content of 10% to 90% of the medicament or of each of its components.

Particularly important are the medicaments of this type, both in anhydrous form (freeze dried powder) or as solutions, concentrated or diluted in water or saline, possibly with the addition of additive or auxillary substances, such as in particular disinfectant substances or mineral salts acting as buffer or others, for ophthalmic use.

Of the medicaments of the invention, particularly important, as the case may be, are those with a degree of acidity suitable for the environment to which they are to be applied, that is with a physiologically tolerable pH. Adjustment of the pH, for example in the above mentioned salts of the esters of hyaluronic acid with a basic active substance, may be effected by suitably regulating the quantities of polysaccharide, of the salts of the basic substance itself. Thus, for example, if the acidity of a salt of a hyaluronic ester with a basic substance is too high, the excess of free acid groups is neutralized with the above mentioned inorganic bases, for example with sodium, potassium or ammonium hydrate.

The preparation of the salts according to the invention may be effected in a per se known manner by placing in contact solutions, aqueous solutions or organic solutions, of the two components (1) and (2), and possibly bases or basic salts of the above mentioned alkaline or alkaline earth metals or magnesium or aluminum in the right quantities and isolating the salts in an amorphous anhydrous form according to known techniques. It is possible for example to prepare first aqueous solutions of the two components (1) and (2), freeing such components from aqueous solutions of their salts with suitable ionic exchangers, and mixing the two solutions at a low temperature, for example between 0° C. and 20° C. If the salt thus obtained is easily soluble in water it can be freeze dried, while the salts which are difficult to solubilize may be separated by centrifugation, filtration or decantation and possibly subsequently dried.

For these associated medicaments too, the dose is based on that of the active principles used singly and may therefore easily be determined by a skilled person, taking into consideration the dosages recommended for the corresponding known drugs.

In the cosmetic articles according to the invention the hyaluronic esters and their salts are mixed with the excipients commonly used in the field and are for example those already listed above for the pharmaceutical preparations. Mostly used are creams, ointments, and lotions for topical use in which the hyaluronic ester or one of its salts may represent the cosmetic active principle possibly with the addition of other cosmetically active principles, such as for example steroids, for example pregnenolone, or one of the principles mentioned above. In such preparations the hyaluronic ester is preferably an ester with an alcohol with no cosmetic action, such as an lower aliphatic alcohol, such as one of those already mentioned. The effect is due to the intrinsic cosmetic properties of the polysaccharide component, such as in the case of free hyaluronic acid or of its salts.

The cosmetic articles may however be based on substances with specific actions other than those of hyaluronic acid, for example disinfectant substances, sunshields, waterproofing or regenerating or antiwrinkle substances, or odorants, especially perfumes. In this case the hyaluronic ester may itself be the active ingredient and derives from alcohols with the same properties, for example from higher aliphatic alcohols or terpenic alcohols in the case of perfumes or acts above all as vehicle for substances with those properties associated with it.

Particularly important therefore are cosmetic compositions similar to the medicaments described above in which the pharmaceutically active component (1) is substituted by a cosmetic factor, and the relative salts.

The use of the above mentioned esters deriving from alcohols used in the perfume industry represent an important step forward in technology, since they allow a slow, constant and protracted release of the scented ingredients.

An important application of the present invention regards sanitary and surgical articles already described above, the methods for their manufacture and use. The invention therefore includes all the articles similar to those already on the market, based on hyaluronic acid but containing a hyaluronic ester or one of its salts in place of the free acid or one of its salts, for example inserts or ophthalmic lenses.

Completely new surgical and sanitary articles according to the present invention are represented by the esters of hyaluronic acid regenerated as such by appropriate organic solutions from which it is possible to obtain, by means of the suitable procedures, films, thin sheets or threads to be used in surgery, as aids or substitutes of the skin in cases of serious damage to this organ, such as for example following burns, as a suture in surgical operations. The invention includes particularly these uses and a procedure for the preparation of such articles consisting in the formation of a solution of hyaluronic ester or of one of its salts in a suitable organic solvent such as an amide of a carboxylic acid, especially a dialkylamide of an aliphatic acid with between 1 and 5 carbon atoms and deriving from alkyl groups with between 1 and 6 carbon atoms, and above all from an organic sulphoxide, that is a dialkylsulphoxide with alkyl groups with a maximum of 6 carbon atoms, such as especially dimethylsulphoxide or diethylsuphoxide and again most importantly by a fluoronated solvent with a lower boiling point such as especially hexafluoro-isopropanol. The invention includes turning such solutions into sheet or thread form and in removing the organic solvent by contact with another organic or aqueous solvent which can be mixed with the first solvent and in which the hyaluronic ester is not soluble, especially a lower aliphatic alcohol, for example ethyl alcohol (wet spinning), or, should a solvent with a not too high boiling point be used to prepare the solution of the hyaluronic derivative, in removing such a solvent in dry conditions with a current of gas, especially with suitably heated nitrogen (dry spinning). It is also possible to obtain excellent results with dry-wet spinning.

The threads obtained with hyaluronic acid esters may be used for the preparation of gauzes for the medication of wounds and in surgery. The use of such gauzes has the except ional advantage of their biodegradability in the organism, made possible by the enzymes which they contain. These enzymes divide the ester into hyaluronic acid and the corresponding alcohol, and therefore into a compound already present in the organism, made possible by the enzymes which they contain. These enzymes divide the ester into hyaluronic acid and the corresponding alcohol, and therefore into a compound already present in the organism and into a harmless compound, such as an alcohol, should a hyaluronic ester be used which derives from a therapeutically acceptable alcohol, such as ethyl alcohol.

These gauzes and also the aforementioned threads may therefore be left inside the organism after surgery, since they are slowly absorbed thanks to the aforesaid degradation.

During the preparation of the sanitary and surgical articles described above, it is possible to add plastifying materials which improve their mechanical characteristics, such as in the case of the threads, to improve their resistance to knots. These plastifying materials may be for example alkaline salts of fatty acids, for example sodium stearate or sodium palmitate, the esters of organic acids with many carbon atoms, etc.

Another application of the new esters, using to advantage their biodegradability due to the esterases present in the organism, is represented by the preparation of capsules for subcutaneous implantation of medicaments or of microcapsules for injection, for example by subcutaneous or intramuscular route. For the applications of subcutaneous medicaments for obtaining a slow release and therefore a "retard" action, capsules made of silicone materials have mostly been used up till now, with the disadvantage that the capsule is liable to move about inside the organism and it is not possible to recover it. Evidently with the new hyaluronic esters this danger no longer exists.

Of great importance is also the preparation of microcapsules made with hyaluronic esters, eliminating the problems regarding their use which up till now has been limited, for the same reasons as those mentioned above and which opens up a vast field of application where a "retard" effect is sought be an injected route.

A further application in the sector of medicine and surgery of the new esters concerns the preparation of a large variety of solid inserts such as plates, discs, sheets, etc. substituting those in metallic form or those made of synthetic plastic materials already in use, in the case of inserts intended for removal after a certain period of time. Preparations made of animal pollagen, being of a proteic nature, often provoke undesirable side effects such as inflammation or rejection. In the case of animal, and not human, hyaluronic acid, this danger does not exist, as there is no incompatability between the polysaccharides of different animal species.

Another application relates to the use to augment and correct soft tissue defects. The need for a safe and effective biomaterial by which to replace missing or damaged soft tissue has long been recognized. Several alloplastic materials, including paraffin, Teflon paste, silicone and borine collagen have been used to replace lost soft tissue. However, these materials have been associated with permanent undesirable textural changes in the skin, with migration from the site of implantation and with adverse treatment reactions. Thus, the need for a versatile biomaterial in medicine continues. The hyaluronic acid esters can be used safely and effectively to augment and correct such soft tissue defects as acne scars, atrophy post surgical irregularities, mohs chemiosurgery, cleft lip sears and age-related wrinkles.

Part of the applications in the field of medicine and surgery of the new esters according to the present invention, are represented by expansive materials, especially in the form of sponges, for the medication of wounds and various lesions.

The following are particular exemplary pharmaceutical preparations according to the invention.

Formulation 1—Collirium containing cortisone of which 100 ml contain:
partial ester of hyaluronic acid with cortisone (Ex. 10), gr. 0.200
ethyl p. hydroxybenzoate, gr. 0.010
methyl p. hydroxybenzoate, gr. 0.050
sodium chloride, gr. 0.900
water for injectable preparations/q.b.a., ml. 100

Formulation 2—Injectable solution containing hydrocortisone of which 100 ml contain:
partial ester of hyaluronic acid with hydrocortisone (Ex. 11), gr. 0.1
sodium chloride, gr. 0.9
water for injectable preparations/q.b.a., ml. 100

Formulation 3—Cream containing a partial ester of hyaluronic acid with ethyl alcohol (Ex. 3), of which 100 gr. contain:
partial ester of hyaluronic acid with ethyl alcohol, gr. 0.2
Polyethylenglycol monostearate 400, gr. 10.000
Cetiol V, gr. 5.000
Lanette SX, gr. 2.000
Paraoxybenzoate of methyl, gr. 0.075
Paraoxybenzoate of propyl, gr. 0.050
Sodium dihydroacetate, gr. 0.100
Glycerine F.U., gr. 1.500
Sorbitol 70, gr. 1.500
Test cream, gr. 0.050
Water for injectable preparations/q.b.a., gr. 100.00

The following are exemplary material products utilizing the hyaluronic esters of the invention.

EXAMPLE 39

Preparation of films using esters of hyaluronic acid

A solution is prepared in dimethylsulfoxide of the n-propyl ester of HY (MW 130,000) with a concentration of 180 mg/ml.

By means of a stratifier, a thin layer of solution is spread on a glass sheet; the thickness must be 10 times greater than the final thickness of the film. The glass sheet is immersed in ethanol which absorbs the dimethylsulfoxide but does not solubilize the HY ester which becomes solid. The film is detached from the glass sheet, is repeatedly washed with ethanol, then with water and then again with ethanol.

The resulting sheet is dried in a press for 48 hours at 30°.

EXAMPLE 40

Preparation of threads using esters of hyaluronic acid

A solution is prepared in dimethylsulfoxide of the benzyl ester of HY (MW 165,000) with a concentration of 200 mg/ml. The solution thus obtained is pressed by means of a pump through a threader with 0.5 mm holes.

The threader is immersed in ethanol/dimethylsulfoxide 80:20 (this concentration is kept constant by continuous addition of ethanol); when the solution in dimethylsulfoxide is soaked in this way it tends to lose most of the dimethylsulfoxide and the thread solidifies.

The thread is stretched while it still has a content of dimethylsulfoxide, is then repeatedly stretched and washed with ethanol. The thread is dried in nitrogen current.

EXAMPLE 41

Preparation of a spongy material made with hyaluronic acid esters 1 g of benzyl ester of hyaluronic acid with a molecular weight of 170,000 in which all the carboxylic groups are esterified (obtained for example as described in Example 14) are dissolved in 5 ml of dimethylsulfoxide. To each 10 ml of solution prepared, a mixture of 31.5 g of sodium chloride with a degree of granularity corresponding to 300μ, 1.28 g of sodium bicarbonate and 1 g of citric acid is added and the whole is homogenized in a mixer.

The pasty mixture is stratified in various ways, for instance by means of a mange consisting of two rollers which turn opposite each other at an adjustable distance between the two. Regulating this distance the paste is passed between the rollers together with a strip of silicone paper which acts as a support to the layer of paste thus formed. The layer is cut to the desired dimensions of length and breadth, removed from the silicone, wrapped in filter paper and emerged in a suitable solvent, such as water. The sponges thus obtained, are washed with a suitable solvent such as water and possibly sterilized with gamma rays.

EXAMPLE 42

Preparation of a spongyv material made with hyaluronic acid esters

In the manner described in Example 41, it is possible to prepare spongy materials with other hyaluronic acid esters. In the place of dimethylsulfoxide it is possible to use, if desired, any other solvent capable of dissolving the chosen ester. In the place of sodium chloride it is possible to use any other solid compound which is insoluble in the solvent used to dissolve the hyaluronic acid ester, but which is however soluble in the solvent used to precipitate the hyaluronic ester after the above mentioned mechanical treatment, and finally which has the correct degree of granularity to obtain the type of pores desired in the sponge material.

In the place of sodium bicarbonate and citric acid it is possible to use other couples of similar compounds, that is, compound which react to each other in suspension or solution of the solvent used to dissolve hyaluronic acid in such a way as to form a gas, such as carbon dioxide, which has the effect of producing a less compact spongy material. In this way it is possible to use, in the place of sodium bicarbonate, other bicarbonates or alkaline or alkaline earth carbonates and in the place of citric acid other acids in solid form, such as tartaric acid.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A partial ester of hyaluronic acid with an alcohol of the aliphatic, araliphatic, cycloaliphatic or heterocyclic series wherein at least a first portion of the carboxylic acid groups of said hyaluronic acid are salified with a therapeutically active amine.

2. A partial ester of hyaluronic acid according to claim 1, wherein a second portion of the carboxylic acid groups of said hyaluronic acid is salified with an alkaline or alkaline earth metal, magnesium or aluminum.

3. A partial ester of hyaluronic acid according to claim 1, wherein said therapeutically active amine is a member selected from the group consisting of alkaloids, peptides, phenothiazines, benzodiazepines, thioxanthenes, hormones, vitamins, anticonvulsants, antipsychotics, antiemetics, anesthetics, hypnotics, anorexics, tranquilizers, muscle relaxants, coronary vasodilators, antineoplastics, antibiotics, antibacterials, antivirals, antimaralarials, carbonci anhydrase inhibitors, nonsteroid antiinflammatory agents, vasoconstrictors, cholinergic agonists, cholinergic antagonists, adrenergic agonists, adrenergic antagonists, and narcotic antagonists.

4. A partial ester according to claim 1, which is in the form of a microcapsule.

5. A partial ester according to claim 3, which is in the form of a microcapsule.

* * * * *